US010317387B2

United States Patent
Vilkov et al.

(10) Patent No.: US 10,317,387 B2
(45) Date of Patent: *Jun. 11, 2019

(54) CHEMICAL VAPORIZATION AND DETECTION OF COMPOUNDS HAVING LOW VOLATILITY

(71) Applicant: Rapiscan Systems, Inc., Torrance, CA (US)

(72) Inventors: Andrey N. Vilkov, Aliso Viejo, CA (US); Joseph A. Widjaja, Laguna Hills, CA (US); Karl A. Hanold, Huntington Beach, CA (US); Jack A. Syage, Corona del Mar, CA (US)

(73) Assignee: Rapiscan Systems, Inc., Torrance, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/599,711

(22) Filed: May 19, 2017

(65) Prior Publication Data

US 2017/0261484 A1    Sep. 14, 2017

Related U.S. Application Data

(63) Continuation of application No. 15/064,203, filed on Mar. 8, 2016, now Pat. No. 9,683,981.

(51) Int. Cl.
*G01N 33/22* (2006.01)
*G01N 33/00* (2006.01)
(Continued)

(52) U.S. Cl.
CPC ............. *G01N 33/227* (2013.01); *G01N 1/22* (2013.01); *G01N 1/405* (2013.01); *G01N 1/4022* (2013.01);
(Continued)

(58) Field of Classification Search
CPC .. G01N 33/0057; G01N 33/22; G01N 33/227; G01N 1/22; G01N 1/4022;
(Continued)

(56) References Cited

U.S. PATENT DOCUMENTS 4,740,356 A * 4/1988 Huber ................ G01N 21/3103
                                                    137/624.18
5,465,607 A    11/1995 Corrigan et al.
(Continued)

FOREIGN PATENT DOCUMENTS

AT    303589 T    9/2005
AT    480769 T    9/2010
(Continued)

OTHER PUBLICATIONS

Peng et al. Scientific Reports, vol. 4: 6631, pp. 1-5, Oct. 16, 2014.
(Continued)

*Primary Examiner* — Maureen Wallenhorst
(74) *Attorney, Agent, or Firm* — Novel IP

(57) ABSTRACT

The present disclosure is directed to methods and systems for detecting a chemical substance. The methods and systems include chemically modifying a sample of a substance of interest through combination with a reagent to increase the volatility of the substance of interest. The systems and methods further include performing an analysis of the substance of interest.

11 Claims, 12 Drawing Sheets

(51) Int. Cl.
*G01N 1/22* (2006.01)
*G01N 1/40* (2006.01)
*G01N 1/02* (2006.01)
*H01J 49/04* (2006.01)

(52) U.S. Cl.
CPC ....... *G01N 1/4044* (2013.01); *G01N 33/0057* (2013.01); *G01N 2001/022* (2013.01); *G01N 2001/028* (2013.01); *H01J 49/049* (2013.01); *H01J 49/0459* (2013.01); *Y10T 436/163333* (2015.01); *Y10T 436/173076* (2015.01); *Y10T 436/25875* (2015.01)

(58) Field of Classification Search
CPC ........... G01N 1/4044; G01N 2001/022; G01N 2001/028; G01N 1/405; Y10T 436/15; Y10T 436/156666; Y10T 436/16; Y10T 436/163333; Y10T 436/173076; Y10T 436/19; Y10T 436/24; Y10T 436/25; Y10T 436/25875; H01J 49/0459; H01J 49/049
USPC ......... 436/79, 100, 102, 103, 104, 110, 124, 436/147, 173, 174, 181; 422/411, 418, 422/83
See application file for complete search history.

(56) References Cited

U.S. PATENT DOCUMENTS

| | | | |
|---|---|---|---|
| 5,491,337 A | 2/1996 | Jenkins | |
| 6,211,516 B1 | 4/2001 | Syage | |
| 6,326,615 B1 | 12/2001 | Syage | |
| 6,329,653 B1 | 12/2001 | Syage | |
| 6,630,664 B1 | 10/2003 | Syage | |
| 6,642,513 B1 | 11/2003 | Jenkins | |
| 6,690,005 B2 | 2/2004 | Jenkins | |
| 6,708,572 B2 | 3/2004 | Jenkins | |
| 6,737,642 B2 | 5/2004 | Syage | |
| 6,765,198 B2 | 7/2004 | Jenkins | |
| 6,815,670 B2 | 11/2004 | Jenkins | |
| 6,831,273 B2 | 12/2004 | Jenkins | |
| 6,840,122 B1 | 1/2005 | Jenkins | |
| 7,047,829 B2 | 5/2006 | Napoli | |
| 7,109,476 B2 | 9/2006 | Hanold | |
| 7,119,342 B2 | 10/2006 | Syage | |
| 7,141,786 B2 | 11/2006 | McGann | |
| 7,161,144 B2 | 1/2007 | Syage | |
| 7,196,325 B2 | 3/2007 | Syage | |
| 7,253,727 B2 | 8/2007 | Jenkins | |
| 7,299,710 B2 | 11/2007 | Syage | |
| 7,338,638 B2 | 3/2008 | McGann | |
| 7,401,498 B2 | 7/2008 | Syage | |
| 7,448,248 B2 | 11/2008 | Carey | |
| 7,456,393 B2 | 11/2008 | Napoli | |
| 7,528,367 B2 | 5/2009 | Haigh | |
| 7,541,577 B2 | 6/2009 | Davenport | |
| 7,594,422 B2 | 9/2009 | Perry | |
| 7,594,447 B2 | 9/2009 | Napoli | |
| 7,663,099 B2 | 2/2010 | Reda | |
| 7,721,588 B2 | 5/2010 | Perry | |
| 7,820,965 B2 | 10/2010 | Nagano et al. | |
| 7,856,898 B2 | 12/2010 | Carey | |
| 7,880,137 B2 | 2/2011 | McGann | |
| 8,161,830 B2 | 4/2012 | Boudries | |
| 8,186,234 B2 | 5/2012 | Syage | |
| 8,288,735 B2 | 10/2012 | Syage | |
| 8,402,842 B2 | 3/2013 | Syage | |
| 8,434,375 B1 | 5/2013 | Syage | |
| 8,614,582 B2 | 12/2013 | Syage | |
| 8,686,355 B2 | 4/2014 | Patterson | |
| 8,723,111 B2 | 5/2014 | Syage | |
| 8,857,278 B2 | 10/2014 | Syage | |
| 8,866,073 B2 | 10/2014 | Goedecke | |
| 8,952,327 B2 | 2/2015 | Patterson | |
| 9,147,565 B1 | 9/2015 | Goedecke | |
| 9,354,153 B2 | 5/2016 | Syage | |
| 9,482,655 B2 | 11/2016 | Vilkov | |
| 9,528,969 B2 | 12/2016 | Shaw | |
| 9,558,924 B2 | 1/2017 | Syage | |
| 9,683,981 B1* | 6/2017 | Vilkov | G01N 33/227 |
| 9,689,857 B1* | 6/2017 | Vilkov | G01N 33/227 |
| 9,726,655 B2 | 8/2017 | Syage | |
| 9,766,218 B2 | 9/2017 | Lai | |
| 9,789,434 B1 | 10/2017 | Lai | |
| 2008/0264186 A1 | 10/2008 | Nacson et al. | |
| 2014/0030816 A1 | 1/2014 | Gregory et al. | |
| 2014/0322518 A1 | 10/2014 | Addleman et al. | |
| 2015/0004710 A1 | 1/2015 | Gregory et al. | |
| 2015/0285780 A1 | 10/2015 | Kelley et al. | |
| 2016/0282304 A1 | 9/2016 | Vilkov | |
| 2017/0103880 A1 | 4/2017 | Syage | |
| 2017/0213715 A1 | 7/2017 | Davila | |
| 2017/0261483 A1 | 9/2017 | Vilkov | |
| 2017/0261484 A1 | 9/2017 | Vilkov | |
| 2017/0284977 A1 | 10/2017 | Rogers | |
| 2017/0309463 A1 | 10/2017 | Vilkov | |
| 2018/0158665 A1 | 6/2018 | Eiceman | |
| 2018/0164189 A1 | 6/2018 | Bilodeau | |
| 2018/0172635 A1 | 6/2018 | Lai | |
| 2018/0172650 A1 | 6/2018 | Platow | |
| 2018/0182603 A1 | 6/2018 | Schmidt | |
| 2018/0182604 A1 | 6/2018 | Lai | |
| 2018/0283993 A1 | 10/2018 | Shaw | |
| 2018/0284081 A1 | 10/2018 | Shaw | |
| 2018/0356320 A1 | 12/2018 | Romanov | |

FOREIGN PATENT DOCUMENTS

| | | |
|---|---|---|
| CA | 2153371 C | 3/1999 |
| CA | 2436256 C | 6/2007 |
| CA | 2382823 C | 11/2007 |
| CA | 2362449 C | 10/2008 |
| CA | 2411532 C | 4/2010 |
| CA | 2285153 C | 5/2010 |
| CA | 2479875 C | 2/2011 |
| CA | 2538709 C | 2/2013 |
| CA | 2790430 A1 | 3/2013 |
| CA | 2807894 A1 | 9/2013 |
| CA | 2620405 C | 7/2014 |
| CA | 2548177 C | 9/2014 |
| CA | 2844222 A1 | 9/2014 |
| CA | 2845959 A1 | 9/2014 |
| CA | 2688352 C | 6/2015 |
| CA | 2644937 C | 11/2015 |
| CA | 2904479 A1 | 3/2016 |
| CA | 2910780 A1 | 4/2016 |
| CA | 2913931 A1 | 6/2016 |
| CA | 2915785 A1 | 6/2016 |
| CA | 2924580 A1 | 9/2016 |
| CA | 2647651 C | 11/2016 |
| CA | 2738053 C | 5/2017 |
| CA | 2959791 A1 | 9/2017 |
| CA | 2959796 A1 | 9/2017 |
| CA | 2962154 A1 | 9/2017 |
| CA | 2964147 A1 | 10/2017 |
| CN | 100445767 C | 12/2008 |
| CN | 103308590 A | 9/2013 |
| CN | 105738461 A | 7/2016 |
| CN | 107037114 A | 8/2017 |
| CN | 107167334 A | 9/2017 |
| CN | 107167335 A | 9/2017 |
| CN | 107271254 A | 10/2017 |
| DE | 69528418 T2 | 1/2003 |
| DE | 69926965 T2 | 6/2006 |
| EP | 2368102 A2 | 9/2011 |
| EP | 2637013 A2 | 9/2013 |
| EP | 2778582 A2 | 9/2014 |
| EP | 2778669 A1 | 9/2014 |
| EP | 2884254 A1 | 6/2015 |
| EP | 3015858 A1 | 5/2016 |
| EP | 3032570 A2 | 6/2016 |
| EP | 3040717 A1 | 7/2016 |

(56) References Cited

FOREIGN PATENT DOCUMENTS

| | | |
|---|---|---|
| EP | 1938078 B1 | 3/2017 |
| EP | 1297554 B1 | 4/2017 |
| EP | 3182111 A1 | 6/2017 |
| ES | 2183855 | 4/2003 |
| FR | 692712 A | 11/1930 |
| GB | 992782 A | 5/1965 |
| GB | 2075578 A | 11/1981 |
| GB | 2496286 A | 5/2013 |
| GB | 2536076 A | 9/2016 |
| JP | 3045655 B2 | 5/2000 |
| WO | 2008067395 A2 | 6/2008 |
| WO | 2014058508 A2 | 4/2014 |

OTHER PUBLICATIONS

Kelley et al., "Reagent approaches for improved detection of chlorate and perchlorate salts via thermal desorption and ionization", Rapid Communications in Mass Spectrometry, Dec. 13, 2015, vol. 30, No. 1, pp. 191-198.
European Search Report for EP 17 00 0312, dated Jul. 4, 2017, 9 pages.
European Search Report for EP 17 00 0313, dated Jul. 4, 2017, 9 pages.
Office Action dated Mar. 14, 2018 for U.S. Appl. No. 15/599,612 (pp. 1-10).
Office Action dated Jul. 31, 2107 for U.S. Appl. No. 15/599,612.
Office Action dated Sep. 11, 2018 for U.S. Appl. No. 15/599,612 (pp. 1-8).

* cited by examiner

CHEMICAL VAPORIZATION AND DETECTION OF COMPOUNDS HAVING LOW VOLATILITY

CROSS-REFERENCE TO RELATED APPLICATIONS

This application is a continuation and claims priority to U.S. patent application Ser. No. 15/064,203, filed Mar. 8, 2016, now U.S. Pat. No. 9,683,981, which is hereby incorporated by reference in its entirety.

BACKGROUND OF THE DISCLOSURE

The embodiments described herein relate generally to a detection technique for chemical substances, and, more particularly, to using reagents to detect contraband substances such as explosives, narcotics, pesticides, and chemical warfare agents by means of spectrometry. More specifically, the methods and systems include chemically modifying a sample of a substance of interest through combination with a reagent to increase the volatility of the substance of interest. The systems and methods further include performing an analysis of the substance of interest.

Certain contraband substances—such as inorganic oxidizer salts—are used in formulations for homemade explosives (HMEs). Examples of classes of these explosives include compounds of nitrates, chlorates, perchlorates and permanganate. These compounds have very low volatility, which makes them difficult to detect by detection systems that rely on vaporization of the sample for detection. Examples of these types of detection systems include mass spectrometry (MS) and ion mobility spectrometry (IMS).

As such, in some instances, detection systems are unable to identify potentially dangerous substances because the substance is not able to be vaporized within the detection system. There remains a need, therefore, for detection systems and methods that use an effective chemical vaporization reagent for use with detection systems that rely on vaporization of the sample that include: (i) effective chemical conversion to a more volatile state of the substance of interest; (ii) low chemical noise to the detector by minimizing the amount of other compounds that may vaporize and interfere or suppress the detector signal; and, (iii) properties that do not adversely affect the detectability of other compounds that need to be detected.

BRIEF DESCRIPTION OF THE DISCLOSURE

In one embodiment of the present disclosure, a method for detecting a substance of interest is disclosed. The method comprises collecting a sample of a substantially non-volatile substance of interest on a sampling trap; depositing a reagent on the trap, wherein the reagent increases the volatility of the substance of interest; introducing the trap including the substance of interest into a thermal desorber; vaporizing the substance of interest; transferring the vaporized substance of interest from the desorber into a detector; performing an analysis of the substance of interest; and, detecting the substance of interest.

In another embodiment of the present disclosure, a method for detecting a substance of interest is disclosed. The method comprises collecting a sample of a substantially non-volatile substance of interest on a sampling trap; introducing the trap including the substance of interest into a thermal desorber; depositing a reagent on the trap within the desorber, wherein the reagent increases the volatility of the substance of interest, wherein depositing the reagent includes spraying the reagent on the trap; vaporizing the substance of interest; transferring the vaporized substance of interest from the desorber into a detector; performing an analysis of the substance of interest; and, detecting the substance of interest.

In yet another embodiment of the present disclosure, a method for detecting a substance of interest is disclosed. The method comprises collecting a sample of a substantially non-volatile substance of interest on a sampling trap; introducing the trap including the substance of interest into a device, wherein the device includes a substantially closed housing and a reservoir including a vaporized reagent; depositing the reagent on the trap, wherein the reagent increases the volatility of the substance of interest, wherein the vaporized reagent is deposited on the trap from the reservoir; introducing the trap including the substance of interest into a thermal desorber; vaporizing the substance of interest; transferring the vaporized substance of interest from the thermal desorber into a detector; performing an analysis of the substance of interest; and, detecting the substance of interest.

In another embodiment of the present disclosure, a method for detecting a substance of interest is disclosed. The method comprises collecting a sample of a substantially non-volatile substance of interest on a sampling trap; introducing the trap including the substance of interest into a thermal desorber, wherein the desorber includes a reagent line coupled to a reagent flow system; depositing the reagent on the trap, wherein the reagent increases the volatility of the substance of interest, wherein the reagent is deposited on the trap through the reagent line; vaporizing the substance of interest; transferring the vaporized substance of interest from the desorber into a detector; performing an analysis of the substance of interest; and, detecting the substance of interest.

In still another embodiment of the present disclosure, a method for detecting a substantially non-volatile salt compound is disclosed. The method comprises collecting a sample of a substantially non-volatile salt compound on a sampling trap, wherein the salt compound includes at least one of sodium nitrate, potassium nitrate, strontium nitrate, barium nitrate, sodium chlorate, potassium chlorate, sodium perchlorate, potassium perchlorate, sodium permanganate, potassium permanganate, and combinations thereof; depositing a reagent on the trap, wherein the reagent increases the volatility of the salt compound; introducing the trap including the salt compound into a thermal desorber; vaporizing the salt compound; transferring the vaporized salt compound from the desorber into a detector; performing an analysis of the salt compound; and, detecting the salt compound.

In yet another embodiment of the present disclosure, a method for detecting a substantially non-volatile salt compound is disclosed. The method comprises collecting a sample of a substantially non-volatile salt compound on a sampling trap, wherein the salt compound includes at least one of sodium nitrate, potassium nitrate, strontium nitrate, barium nitrate, sodium chlorate, potassium chlorate, sodium perchlorate, potassium perchlorate, sodium permanganate, potassium permanganate, and combinations thereof; introducing the trap including the salt compound into a thermal desorber; depositing a reagent on the trap within the desorber, wherein the reagent increases the volatility of the salt compound, wherein depositing the reagent includes spraying the reagent on the trap; vaporizing the salt compound; transferring the vaporized salt compound from the desorber into a detector; performing an analysis of the salt compound; and, detecting the salt compound.

In another embodiment of the present disclosure, a method for detecting a substantially non-volatile salt compound is disclosed. The method comprises collecting a sample of a substantially non-volatile salt compound on a sampling trap, wherein the salt compound includes at least one of sodium nitrate, potassium nitrate, strontium nitrate, barium nitrate, sodium chlorate, potassium chlorate, sodium perchlorate, potassium perchlorate, sodium permanganate, potassium permanganate, and combinations thereof; introducing the trap including the salt compound into a device, wherein the device includes a substantially closed housing and a reservoir including a vaporized reagent; depositing the reagent on the trap, wherein the reagent increases the volatility of the salt compound, wherein the vaporized reagent is deposited on the trap from the reservoir; introducing the trap including the salt compound into a thermal desorber; vaporizing the salt compound; transferring the vaporized salt compound from the thermal desorber into a detector; performing an analysis of the salt compound; and, detecting the salt compound.

In another embodiment of the present disclosure, a method for detecting a substantially non-volatile salt compound is disclosed. The method comprises collecting a sample of a substantially non-volatile salt compound on a sampling trap, wherein the salt compound includes at least one of sodium nitrate, potassium nitrate, strontium nitrate, barium nitrate, sodium chlorate, potassium chlorate, sodium perchlorate, potassium perchlorate, sodium permanganate, potassium permanganate, and combinations thereof; introducing the trap including the salt compound into a thermal desorber, wherein the desorber includes a reagent line coupled to a reagent flow system; depositing the reagent on the trap, wherein the reagent increases the volatility of the salt compound, wherein the reagent is deposited on the trap through the reagent line; vaporizing the salt compound; transferring the vaporized salt compound from the desorber into a detector; performing an analysis of the salt compound; and, detecting the salt compound.

In another embodiment of the present disclosure, a method for detecting a substantially non-volatile salt compound is disclosed. The method comprises increasing the volatility of a substantially non-volatile salt compound, wherein the salt compound includes at least one of sodium nitrate, potassium nitrate, strontium nitrate, barium nitrate, sodium chlorate, potassium chlorate, sodium perchlorate, potassium perchlorate, sodium permanganate, potassium permanganate, and combinations thereof, wherein the volatility of the salt compound is increased by applying a reagent to the salt compound; vaporizing the salt compound in a thermal desorber; and, transferring the vaporized salt compound into a detector, wherein the detector performs an analysis of the vaporized salt compound and detects the salt compound.

In another embodiment of the present disclosure, a substance detection system is disclosed. The system comprises a sampling trap including a substantially non-volatile substance of interest; a deposition device including a reagent, the deposition device configured to deposit the reagent onto the sampling trap, wherein the reagent increases the volatility of the substance of interest; a thermal desorber configured to hold the sampling trap, wherein the desorber is configured to vaporize the substance of interest; and, an analysis device in flow communication with the desorber and configured to receive the vaporized substance of interest and perform an analysis of the substance of interest.

In yet another embodiment of the present disclosure, a substance detection system is disclosed. The system comprises a sampling trap including a substantially non-volatile substance of interest; a thermal desorber configured to hold the sampling trap, wherein the desorber includes a deposition device, the deposition device including a reagent and configured to deposit the reagent onto the sampling trap, wherein the reagent increases the volatility of the substance of interest, wherein the desorber is configured to vaporize the substance of interest; and, an analysis device coupled in flow communication with the desorber, the analysis device configured to receive the vaporized substance of interest and perform an analysis of the substance of interest.

In still another embodiment of the present disclosure, a substance detection system is disclosed. The system comprises a sampling trap including a substantially non-volatile salt compound, wherein the salt compound includes at least one of sodium nitrate, potassium nitrate, strontium nitrate, barium nitrate, sodium chlorate, potassium chlorate, sodium perchlorate, potassium perchlorate, sodium permanganate, potassium permanganate, and combinations thereof; a deposition device including a reagent, the deposition device configured to deposit the reagent onto the sampling trap, wherein the reagent increases the volatility of the salt compound; a thermal desorber configured to hold the sampling trap, wherein the desorber is configured to vaporize the salt compound; and, an analysis device in flow communication with the desorber and configured to receive the vaporized salt compound and perform an analysis of the salt compound.

In yet another embodiment of the present disclosure, a substance detection system is disclosed. The system comprises a sampling trap including a substantially non-volatile salt compound; a thermal desorber configured to hold the sampling trap, wherein the desorber includes a deposition device, the deposition device including a reagent and configured to deposit the reagent onto the sampling trap, wherein the reagent increases the volatility of the salt compound, wherein the desorber is configured to vaporize the salt compound; an analysis device coupled in flow communication with the desorber, the analysis device configured to receive the vaporized salt compound and perform an analysis of the salt compound.

DETAILED DESCRIPTION OF THE DISCLOSURE

Figure 1:
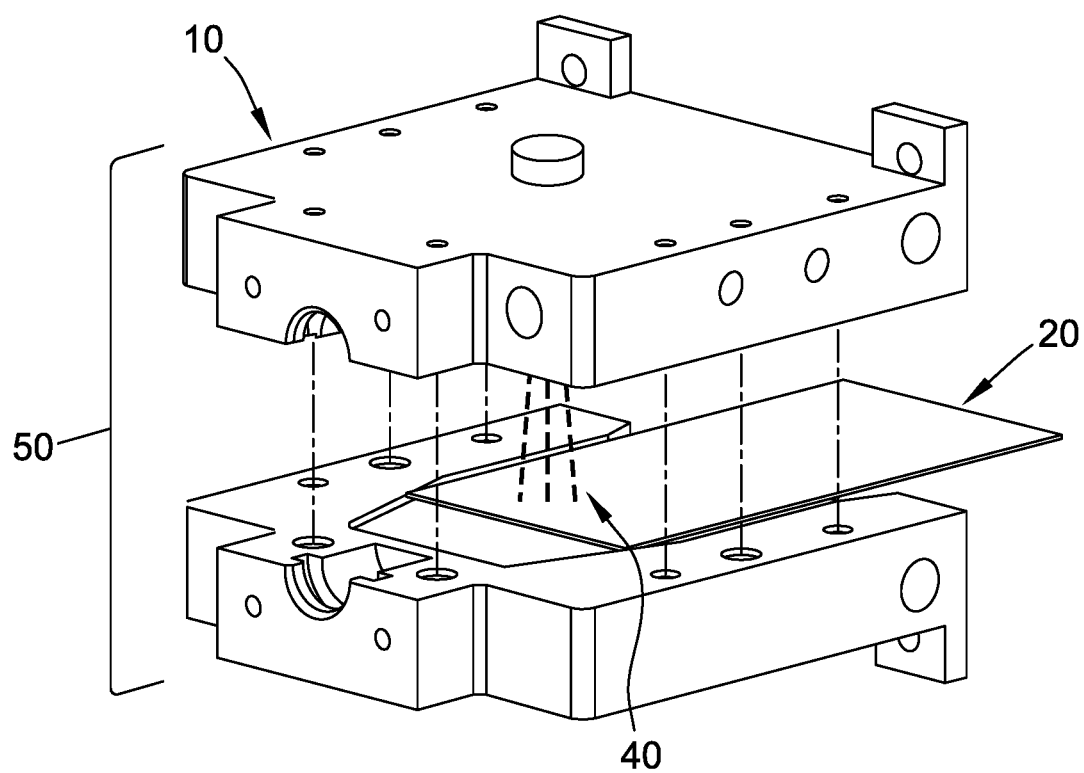
FIG. 1 is an exemplary embodiment of a schematic view of a jet sprayer in a desorber unit of a detection system in accordance with the present disclosure.

The embodiments disclosed herein improve detection of substances of interest (e.g., explosives) through the use of reagents to convert compounds having low and/or no volatility into more volatile compounds that can be vaporized and detected. The embodiments disclosed herein also disclose various methods and devices for modifying a sampling trap used to collect a substance of interest such that the substance of interest can be detected. The application of the chemi-vaporizing material is added by liquid deposits, liquid spray, vapor deposits and is added either before and/or after the swabbing of a surface. In some embodiments, the application of the reagent occurs with or without swabbing a surface, such as, for example, directly applying the reagent to a surface (e.g., a suitcase, article of clothing, etc.). The embodiments disclosed herein also discuss the use of immobilized chemi-vaporizing reagents on the sampling traps in order to be able to re-use the traps and to minimize outgassing of the reagent into a detector of a detection system.

The present disclosure is directed to converting substantially non-volatile substances of interest into a more volatile form so that the substance of interest can be detected through a detection system. As defined herein, the term "substantially non-volatile" includes both substances that completely lack volatility (i.e., are non-volatile) and substances that have a low volatility, including substances that are not capable of being vaporized in a thermal desorber during the normal use and operating conditions of the thermal desorber, such as an ITDX desorber. Volatility is defined as a substance's ability to transform from a solid state to a gaseous state (i.e., vaporized). In some embodiments, a "low volatile" compound includes a compound that is not vaporized at room temperature. In other embodiments, a "low volatile" compound includes a compound that is not vaporized at a temperature of at least about 100° C., at least about 200° C., at least about 300° C., at least about 400° C., at least about 500° C., at least about 600° C. or at least about 700° C. In some embodiments, a "low volatile" compound includes a compound having a vapor pressure of about $10^{-9}$ Torr or below.

Different substances of interest have different levels of volatility. Substances that are substantially non-volatile are difficult to detect in detection systems because they are not readily transformed from their solid state to their vaporized form, and, as such, the detection systems cannot identify the potentially harmful substance of interest. These substantially non-volatile substances often require extremely high temperatures in order to thermally desorb them. In accordance with the present disclosure, the inventors have surprisingly found a way to convert and detect substantially non-volatile compounds into a more volatile form through the use of dry chemistry (i.e., chemical conversion through dry transfers rather than direct deposits of calibrated solutions). Once in a more volatile form, the substances are vaporized in, for example, a thermal desorber and then transferred into a detector for analysis.

The use of dry chemistry to convert the substantially non-volatile substances of interest into a more volatile form is beneficial for use with sampling traps and explosive trace detection devices. This is particularly important for applications where sampling is done by swabbing a surface suspected of having trace residue of contraband, explosives and/or illicit substances. Real world application of sampling traps does not involve the use of liquids and therefore the chemistry is different from reactions using liquid depositions of target compounds.

In some embodiments of the present disclosure, the substantially non-volatile substance of interest includes at least one of an explosive, an energetic material, a taggant, a narcotic, a toxin, a chemical warfare agent, a biological warfare agent, a pollutant, a pesticide, a toxic industrial chemical, a toxic industrial material, a homemade explosive, a pharmaceutical trace contaminant and combinations thereof. In some embodiments, the substantially non-volatile substance of interest includes at least one salt compound, such as, for example, an oxidizer-based salt compound. In some embodiments, the at least one salt compound includes at least one of nitrates, chlorates, perchlorates, permanganates and combinations thereof. In some embodiments, the substantially non-volatile substance of interest includes at least one of sodium nitrate, potassium nitrate, strontium nitrate, barium nitrate, sodium chlorate, potassium chlorate, sodium perchlorate, potassium perchlorate, sodium permanganate, potassium permanganate and combinations thereof.

In some embodiments, the substantially non-volatile substances of interest are reaction products from the combination of acids and bases, which generally have higher volatilities. A means for increasing the volatility of these substantially non-volatile substances is to convert them back to acids and bases. These reactions exist as an equilibrium and thus the addition of other chemicals can shift the equilibrium point. In accordance with the present disclosure, the inventors have surprisingly found a way to shift the equilibrium back toward the more volatile acids and bases.

In accordance with the present disclosure, at least two mechanisms are provided to detect and/or identify the substance of interest. In some embodiments, a reagent is deposited on the substantially non-volatile substance of interest. In some embodiments, the reagent includes an acid, designated as "HY." In some embodiments, the substantially non-volatile substance of interest includes a salt, designated as "XY." In these embodiments, the following reaction occurs:

$$XY(salt)+HA(acid) \rightarrow HY(acid)+XA(salt) \qquad (1).$$

In these embodiments, the acid converts the salt from the structure XY to HY, which is a more volatile form of the salt and thus more easily vaporized and/or detected in the detection system.

In other embodiments, the reagent includes a reducing agent. In these embodiments, the reducing agent (designated as "BC") is deposited on the salt substance of interest and the following reaction occurs:

$$XY(salt)+BC(reducing\ agent) \rightarrow XY[-O]+BOC \qquad (2).$$

In these embodiments, the reducing agent converts the salt XY to a compound XY[—O], which is a more volatile form of the salt and thus more easily vaporized and/or detected in the detection system. The reducing agent also confirms the salt XY or its acid form HY.

Thus, in some embodiments of the present disclosure, the reagent includes an acid. In some embodiments, the reagent includes at least one of an organic acid and an inorganic acid. In some embodiments, the reagent includes at least one of sulfuric acid, sulfonic acid, phosphonic acid, phosphoric acid and combinations thereof.

In other embodiments, the reagent includes a reducing agent. In some embodiments, the reducing agent includes a phosphorous compound, such as, for example, phosphorous trichloride, phosphorous pentachloride, phosphorous oxychloride, diphosphorous tetrachloride, phosphorous triflouride, phosphorous tribromide, phosphorous triiodide, and combinations thereof.

When either an acid or reducing agent are used in accordance with the present disclosure as the reagent, the reagent chemically modifies the substance of interest to increase the volatility of the substance of interest. Once modified with an increased volatility (e.g., in vaporized form), the substance of interest is vaporized and then introduced into a detector of a detection system and an analysis is performed on the substance of interest to detect its presence and/or identify the particular substance.

Table 1, for example, discloses the melting points and boiling points for exemplary salts and their acid counterparts. As can be seen in Table 1, when potassium chlorate is modified into its acidic form, both the melting point and the boiling point are decreased. This, in turn, increases the volatility of the substance of interest, which makes the substance more readily detected and/or identified in a detection system.

TABLE 1

| Compound | Melting Point (C.) | Boiling Point (C.) |
|---|---|---|
| KClO$_3$ | 356 | 400 decomp |
| KClO$_4$ | 525 | 600 decomp |
| HClO$_3$ | N/A | <110 C. |
| HClO$_4$ | −112 | 203 |

Application Methods

The present disclosure is also directed to methods for detecting a substance of interest, including various applications of the chemical modification of the substantially non-volatile substances of interest. The present disclosure is able to overcome known deficiencies by providing embodiments to apply the chemically-modifying reagent in a practical detection device rather than, for example, using a syringe, which is not a practical method for use in either public venues and/or by non-technical users.

The present disclosure also provides embodiments that achieve optimal chemistry changes for the detection of substantially non-volatile substances of interest through a combination of a reagent or reagents, sample conditions, thermal control and combinations thereof. In some embodiments, the effectiveness of the reagent to convert the substantially non-volatile substance of interest into a more volatile form is enhanced by the addition of water. In these embodiments, the reagent is applied in aqueous form in which water vapor from the air binds to the reagent.

In some embodiments, the sampling trap is a medium, such as a strip of material that is handled by a user's (e.g., person's) hand or in a wand device. An exemplary method of use is to hold the sampling medium and rub the medium across a surface to collect a sample. In some embodiments, the collected samples include at least one substance of interest. In other embodiments, the collected samples include more than one substance of interest. In some embodiments, the sampling medium includes polytetrafluoroethylene, a paper material and/or derivatives thereof, and combinations thereof. In some embodiments, the sampling trap is used multiple times, which is beneficial for the economy. It should be understood that in some embodiments of the present disclosure, the "sampling trap" is any medium or means known/used in the art for collecting a sample, such as, but not limited to, a trap, a tray, a strip of material, a wand device, an article of clothing, a piece of luggage, a cotton swab, a piece of paper, a glove, a brush and the like.

In one embodiment, a method for detecting a substance of interest is disclosed, the method comprising collecting a sample of a substantially non-volatile substance of interest on a sampling trap; introducing the trap including the substance of interest into a thermal desorber; depositing a reagent on the trap within the desorber, wherein the reagent increases the volatility of the substance of interest, wherein depositing the reagent includes spraying the reagent on the trap; vaporizing the substance of interest; transferring the vaporized substance of interest from the desorber into a detector; performing an analysis of the substance of interest; and, detecting the substance of interest.

In accordance with the present disclosure, it is understood that the sample can be collected either before or after spraying with the reagent. Thus, in some embodiments, an exemplary method would include collecting a sample by, for example, wiping an article of clothing of a user and then introducing the reagent to the sample. In other embodiments, the reagent is introduced, for example, onto the sample on the article of clothing and then collected by the sampling trap.

In some embodiments, the detector of the present disclosure includes at least one of an ion mobility spectrometer (IMS), an ion trap mobility spectrometer (ITMS), a drift spectrometer (DS), a non-linear drift spectrometer, a field ion spectrometer (FIS), a radio frequency ion mobility increment spectrometer (IMIS), a field asymmetric ion mobility spectrometer (FAIMS), an ultra-high-field FAIMS, a differential ion mobility spectrometer (DIMS) and a differential mobility spectrometer (DMS), a traveling wave ion mobility spectrometer, a semiconductor gas sensor, a Raman spectrometer, a laser diode detector, a mass spectrometer (MS), a gas chromatograph (GC), an electron capture detector, a photoionization detector, a chemiluminescence-based detector, an electrochemical sensor, an infrared spectrometer, a lab-on-a-chip detector and combinations thereof.

In previously known methods, a sampling trap is inserted into a desorber and compounds that were collected were vaporized and entered into the detection system. Because these different compounds have different properties of volatilization, however, they will thermally desorb at different times and for different amounts of time. Therefore, the insertion time and the analysis time are set to ensure that all compounds have sufficiently desorbed to be detected. In some embodiments, however, the substantially non-volatile compounds will not desorb by this method alone. The deposition of the reagent therefore is needed and in some embodiments a spray device is implemented in the thermal desorber to deposit the reagent to enhance the detection of these compounds. In some embodiments, the spray is implemented at the beginning of the sample insertion period, at the end of the insertion period, or any time in between. In some embodiments, the spray is applied at the end of the analysis period after the normally detected, more volatile compounds have been vaporized and detected.

FIG. 1 discloses an exemplary embodiment of the present disclosure, wherein the sampling trap is introduced into a thermal desorber, and then a reagent is sprayed from a jet within the thermal desorber onto the sampling trap to chemically modify the substance of interest to increase the volatility of the substance of interest.

Figure 2:
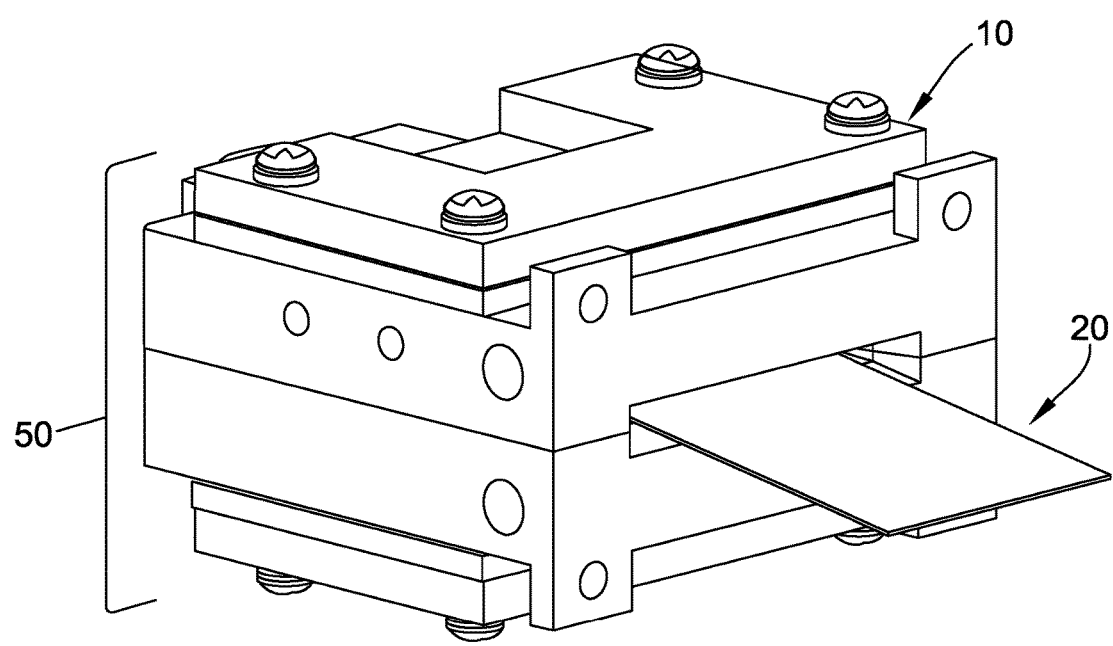
FIG. 2 is an exemplary embodiment of a desorber unit of a detection system in accordance with the present disclosure.

FIG. 1 depicts an exemplary embodiment of a desorber in accordance with the present disclosure. The desorber 10 is shown as separated into two halves of desorber plates 50. A sampling trap 20 including a sample that includes at least one substance of interest is inserted into the desorber 10. In some embodiments, the sampling trap 20 is a swab, a sample coupon, a preconcentrator device, and other devices known in the industry for collecting samples. Once the sampling trap 20 is at least partially within the desorber 10, a spray 40 including a reagent is sprayed onto the sampling trap 20. FIG. 2 is an exemplary embodiment of this method with a view of the desorber 10 in operation, where the spray cannot be seen from the outside of the desorber 10.

In another embodiment of the present disclosure, the method comprises applying the reagent to the sampling trap outside of the desorber. Specifically, the method comprises collecting a sample of a substantially non-volatile substance of interest on a sampling trap; depositing a reagent on the trap, wherein the reagent increases the volatility of the substance of interest; introducing the trap including the substance of interest into a thermal desorber; vaporizing the substance of interest; transferring the vaporized substance of interest from the desorber into a detector; performing an analysis of the substance of interest; and, detecting the substance of interest.

In some embodiments, the method comprises spraying the trap with the reagent. In some embodiments, the trap is sprayed with the reagent prior to collecting the substance of interest. In other embodiments, the trap is sprayed with the reagent after collecting the substance of interest. In some embodiments, the trap is sprayed with at least one of a bottle, a calibrated volumetric spray, a standoff device, within a housing and combinations thereof.

Figure 4:
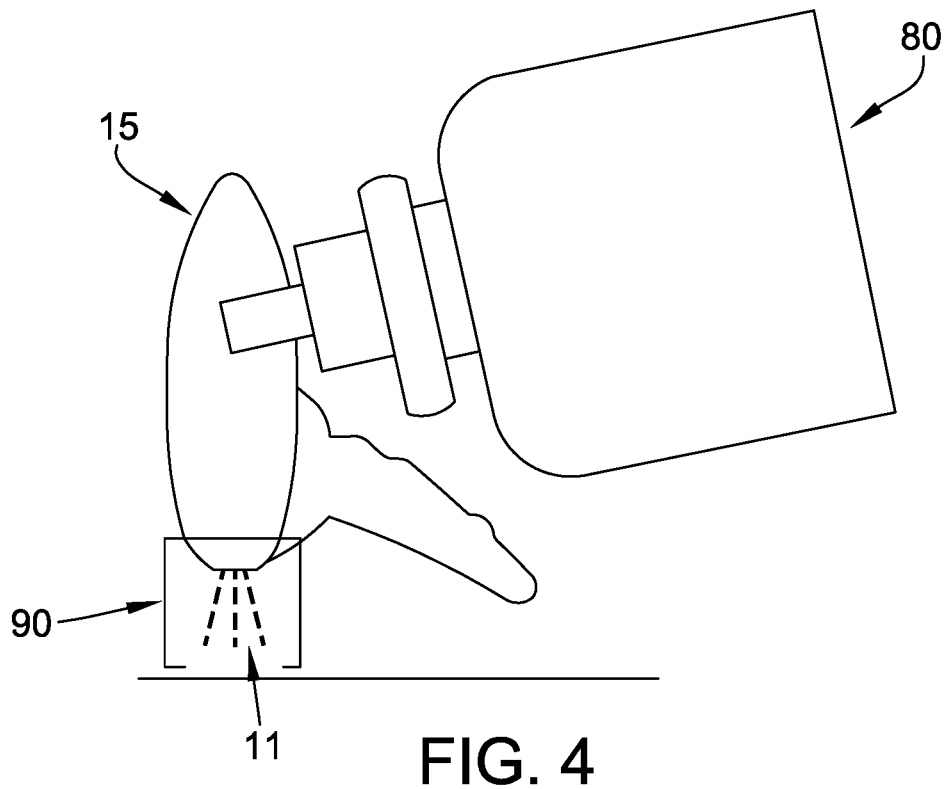
FIG. 4 is an exemplary embodiment of a schematic view of a bottle sprayer in accordance with the present disclosure.
Figure 5:
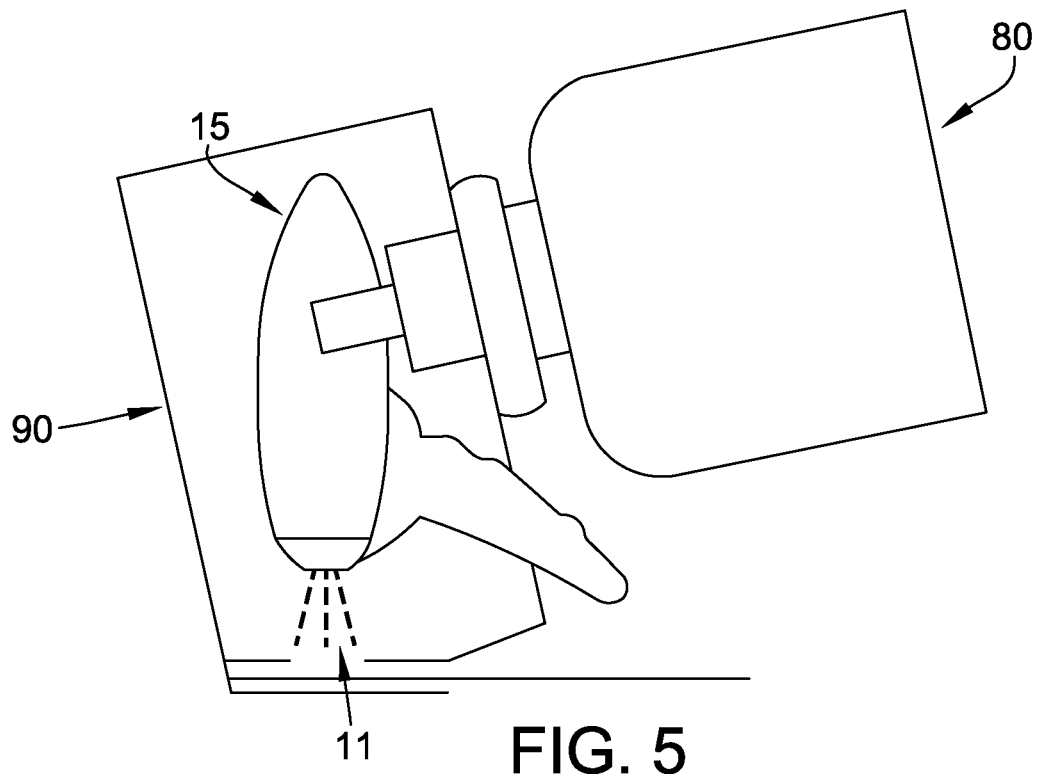
FIG. 5 is an exemplary embodiment of a schematic view of a bottle sprayer in accordance with the present disclosure.
Figure 6:
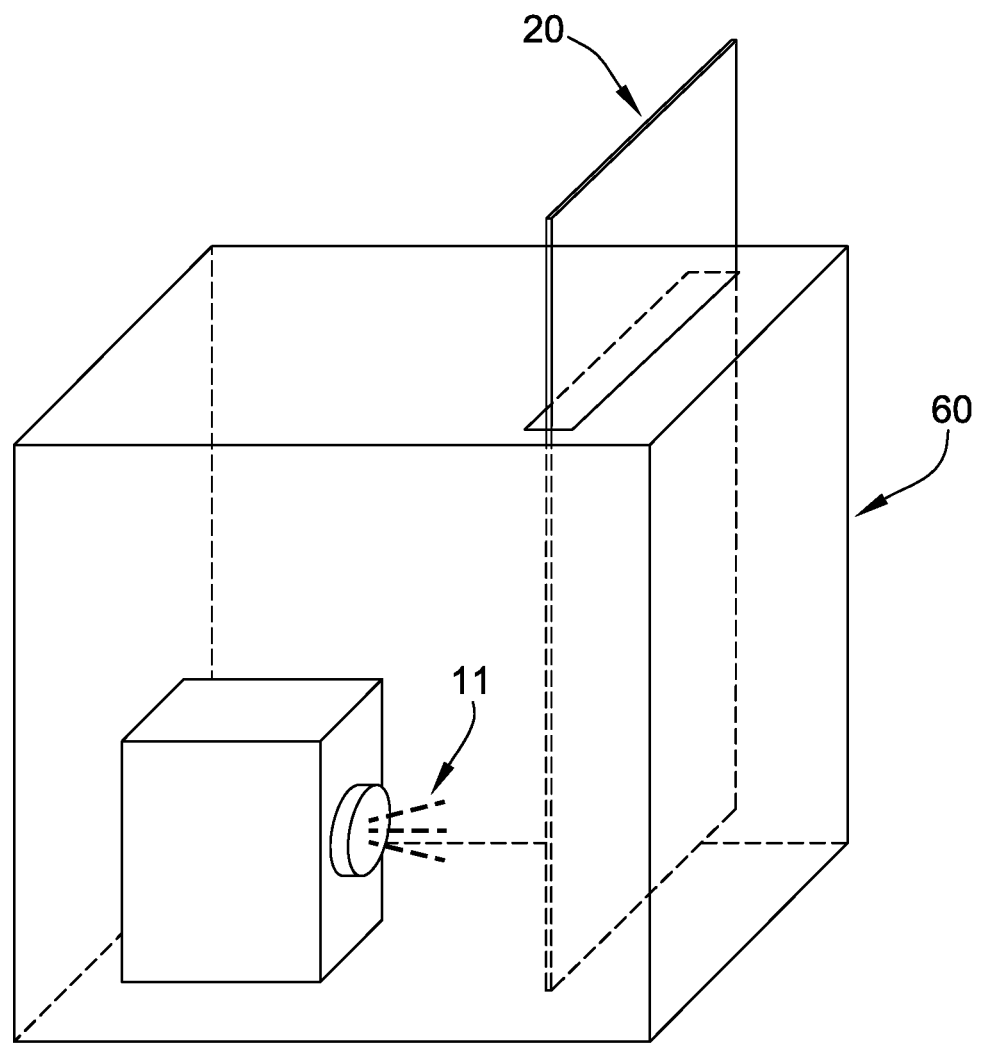
FIG. 6 is an exemplary embodiment of a device including a sprayer in accordance with the present disclosure.

FIGS. 4-6 disclose exemplary methods that use a spray bottle or spritzing device containing acid or reducing agent reagents that increase the volatility of the substance of interest. It is important that the device delivers a spray of a desired volume and applied evenly over an area of the sampling medium for which target compounds are collected. In some embodiments, the effective sampling area includes an area caused by the depression of a thumb when screening a surface. In some embodiments, the area is about one cubic centimeter.

For an acid reagent such as $H_2SO_4$, which is a strong acid, the mass of pure acid required is about 1 microgram. This corresponds to an aqueous solution of about 1 microliter for a solution at a purity of about 0.2%. For a weaker acid such as $NaHSO_4$, a higher concentration aqueous solution is required. In these cases, a spray device dispenses about 1 microliter over about 1 cubic centimeter. This is achieved with a calibrated spray nozzle placed at an appropriate distance from the sampling medium as shown in FIG. 4. It is desirable to keep the volume of the spray to a minimum to minimize the amount of water that eventually desorbs in the thermal desorber of the analyzer.

FIG. 4 is an exemplary embodiment wherein a bottle 80 includes a spray nozzle 15 and a housing 90 surrounding the area of the spray nozzle 15 where the reagent 11 exits. FIG. 5 discloses an alternative embodiment wherein the entire spray nozzle 15 of the bottle 80 is enclosed within the housing 90 when applying the reagent 11 to the sample trap. FIG. 6 discloses another alternative embodiment wherein the sample trap 20 is inserted into a substantially closed housing 60 and then the reagent 11 is sprayed on the sampling trap 20 to chemically modify and increase the volatility of the substance of interest.

Thus, in the embodiments described in FIGS. 4-6, the reagent is deposited on the sampling trap prior to being inserted into the thermal desorber. The sampling trap is then introduced into the thermal desorber, where the chemically-modified substance of interest, now having an increased volatility after the reagent is sprayed onto the substance, is vaporized and then transferred into the detector. As a result of the increased volatility, the substance of interest is able to be vaporized and then detected within the detector after performing an analysis on the chemically-modified form of the substance of interest.

In accordance with the present disclosure, multiple methods are used to enhance the detection of the substantially non-volatile substance of interest. For example, in some embodiments, instead of using a sprayer device to deposit the reagent, a vapor pressure deposition device is used. Thus, in another embodiment of the present disclosure, the method of detecting a substance of interest comprises collecting a sample of a substantially non-volatile substance of interest on a sampling trap; introducing the trap including the substance of interest into a device, wherein the device includes a substantially closed housing and a reservoir including a vaporized reagent; depositing the reagent on the trap, wherein the reagent increases the volatility of the substance of interest, wherein the vaporized reagent is deposited on the trap from the reservoir; introducing the trap including the substance of interest into a thermal desorber; vaporizing the substance of interest; transferring the vaporized substance of interest from the thermal desorber into a detector; performing an analysis of the substance of interest; and, detecting the substance of interest.

As used herein, the phrase "substantially closed housing" refers to a housing that is either completely closed or only allows a minimal amount of air to enter into the housing. Thus, in some embodiments, the housing includes a seal that prevents air and other components from outside of the housing from entering the housing. The trap is then inserted through the seal and breaks the seal. When this occurs, however, the trap substantially fills the void of where the seal was broken and thus the housing remains substantially closed such that either no, or very little, outside components (e.g., air) enter the housing.

Figure 3:
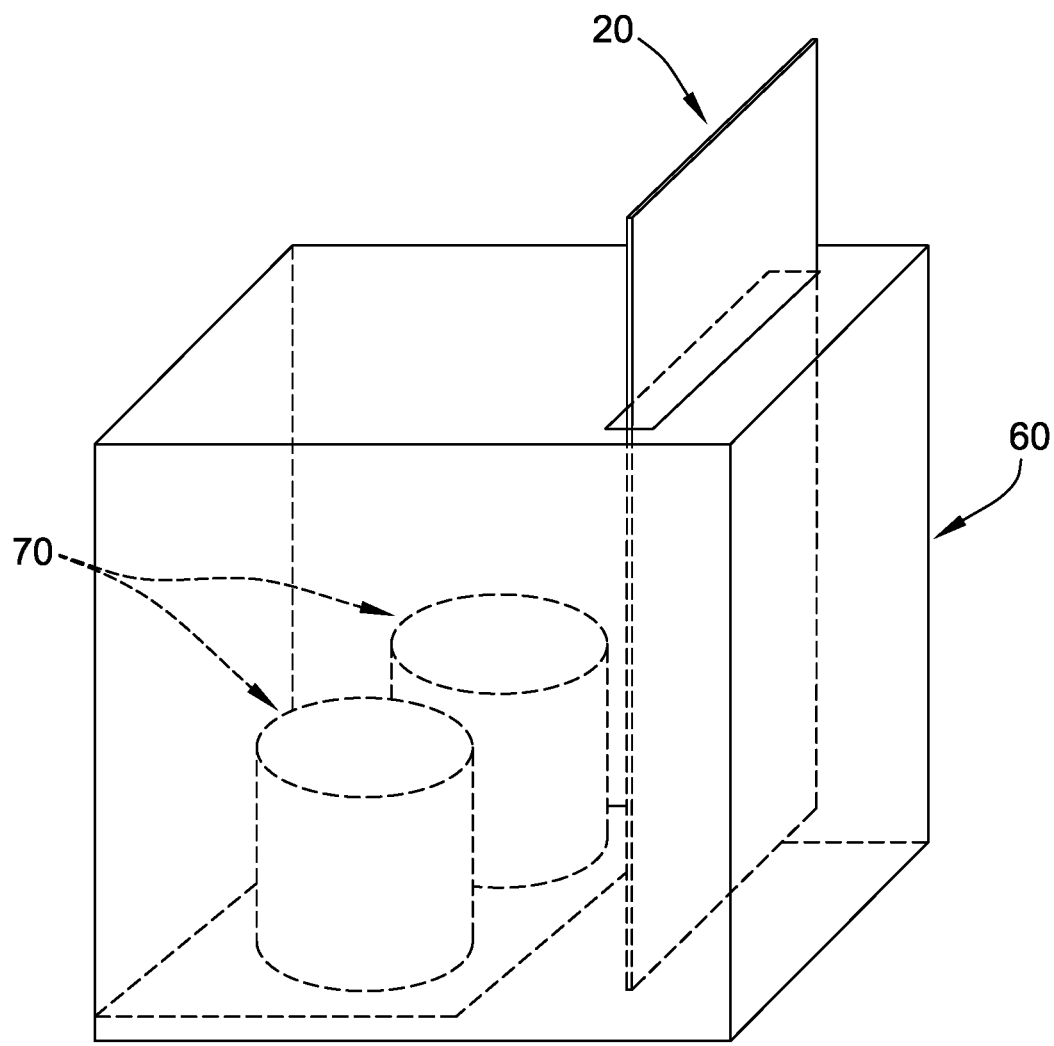
FIG. 3 is an exemplary embodiment of a schematic view of a sample preparation device in accordance with the present disclosure.

FIG. 3 discloses an exemplary embodiment wherein a sampling trap 20 is inserted into a substantially closed housing 60. Within the closed housing 60 is at least one vessel 70 that contains the reagent in vaporized form. The vapor pressure allows the reagent to permeate throughout the housing 60 as a vapor. The sampling trap 20 is inserted into the housing 60 and is in contact with the reagent vapor for an appropriate period of time for the reagent to deposit on the sampling trap 20. In some embodiments, the trap 20 is in contact with the reagent vapor for less than about 15 seconds, less than about 10 seconds, less than about 5 seconds or less than about 2 seconds.

The sampling trap 20 is then removed and inserted into the thermal desorber of the detector. In some embodiments, more than one vessel 70 is used within the housing 60. Additionally, in some embodiments, humidity enhances the chemical modification of the substance of interest within the housing 60. In some embodiments, the vessels 70 are in the form of an open container, a permeation tube, and combinations thereof. In some embodiments, the at least one vessel 70 is heated in order to achieve the desired vapor pressure.

In some embodiments, the vessel is heated to a temperature of up to about 100° C., up to about 200° C., or up to about 300° C. In some embodiments, the heat accelerates the chemical reaction between the reagent and the substance of interest such that the volatility of the substance of interest is increased quicker than without the application of heat. In some embodiments, the vapor pressure within the vessel is at least about 0.1 Torr, at least about 1.0 Torr, or at least about 5.0 Torr.

In another embodiment of the present disclosure, the reagent is introduced into the thermal desorber directly in vapor form. The method comprises collecting a sample of a substantially non-volatile substance of interest on a sampling trap; introducing the trap including the substance of interest into a thermal desorber, wherein the desorber includes a reagent line coupled to a reagent flow system; depositing the reagent on the trap, wherein the reagent increases the volatility of the substance of interest, wherein the reagent is deposited on the trap through the reagent line; vaporizing the substance of interest; transferring the vaporized substance of interest from the desorber into a detector; performing an analysis of the substance of interest; and, detecting the substance of interest.

The reagent is applied directly to the substance of interest on the sampling trap by using a reagent flow system. The reagent flow system includes a vessel and a pump that circulates the reagent vapor across the sampling trap. In some embodiments, a dopant flow system is present, wherein the dopant is used to enhance the ionization process of a substance of interest. In some embodiments, when the dopant flow system is present, the reagent is placed in a dopant reservoir within the dopant flow system. In other embodiments, the reagent is placed parallel to the dopant flow system and then mixed with the preexisting flow of dopant. In some embodiments, the dopant flow begins at the inlet side of the desorber so that the reagent flows across the sampling trap.

Figure 7:
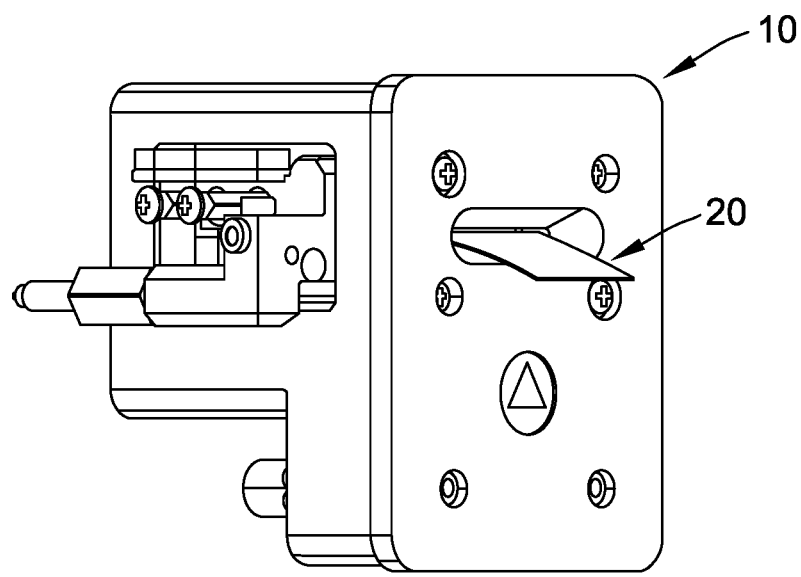
FIG. 7 is an exemplary embodiment of a schematic view of a dopant line to a detection system in accordance with the present disclosure.
Figure 8:
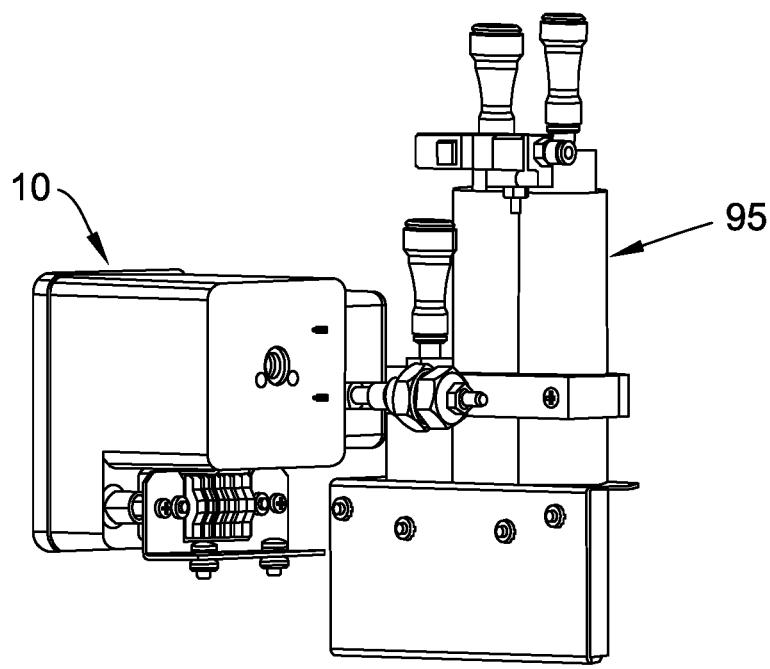
FIG. 8 is an exemplary embodiment of a schematic view of a dopant line to a detection system in accordance with the present disclosure.

FIG. 7 is an exemplary embodiment of a thermal desorber 10 and a sampling trap 20 being inserted therein. As shown in FIG. 8, the desorber is attached to a reagent flow system 95.

In some embodiments of the present disclosure, the reagent is deposited on the trap at a concentration rate of from about 1 cc/min to about 1,000 cc/min, from about 10 cc/min to about 500 cc/min; from about 50 cc/min to about 100 cc/min, and ranges therebetween.

In alternative embodiments of the present disclosure, the process of converting the substantially non-volatile substance of interest into a more volatile form includes using thermal control in the desorber, separating the time periods of desorption, and combinations thereof.

In another embodiment of the present disclosure, a two-step desorption process is used to convert the substantially non-volatile substance of interest into a more volatile form. In particular, the method comprises collecting a sample of a substantially non-volatile substance of interest on a sampling trap; introducing the trap including the substance of interest into a thermal desorber; conducting a two-step desorption process within the desorber of the substance of interest, the two-step desorption process comprising desorbing the salt compound for a first period of time; depositing a reagent on the trap, wherein the reagent increases the volatility of the salt compound, wherein depositing the reagent includes spraying the reagent on the trap; and, desorbing the salt compound for a second period of time, wherein desorbing the substance of interest for a second period of time includes vaporizing the substance of interest; transferring the vaporized substance of interest from the desorber into a detector; performing an analysis of the substance of interest; and, detecting the substance of interest.

Thus, in these embodiments, the sampling trap including the substance of interest is introduced into the desorber and then the substance is thermally desorbed for a first period of time of from about 0 seconds to about 6 seconds, from about 1 second to about 5 seconds, or for about 3 seconds. After this first period of desorption, the reagent is then deposited onto the substance of interest and the substance of interest is then thermally desorbed for a second period of time. In some embodiments, the second period of time of thermal desorption is from about 6 seconds to about 12 seconds, from about 8 seconds to about 10 seconds, or for about 9 seconds.

One of the benefits of the two-step desorption process is that the introduction of the reagent will not interfere with the detection of any additional substances on the sampling trap, including those that are volatile. That is, during the first desorption step, prior to the deposition of the reagent, if any volatile substances of interest are present on the sampling trap that are able to be vaporized through the normal desorption using a standard thermal desorber (e.g., ITDX), these substances are vaporized and transferred to the detector for analysis as their detection would normally occur. Then, subsequent to this process, if any substantially non-volatile substances of interest are on the sampling trap but were not vaporized through the normal use and conditions of the thermal desorber, the reagent is applied to the sampling trap to increase the volatility of the substance of interest and then a second desorption step occurs that will then vaporize and transfer the chemically-modified form of the previously substantially non-volatile substance of interest into the detector to be analyzed and detected by the detector. Thus, an exemplary advantage of using a two-step desorption process in accordance with the present disclosure is the ability to detect both volatile and substantially non-volatile substances of interest located within a single sampling trap.

For some compounds, even when the volatility of the compound has been increased, it is still difficult to vaporize the compound as a result of having a high melting point and/or boiling point (e.g., $KClO_4$). Thus, in some embodiments of the present disclosure, the substantially non-volatile substances of interest are chemically modified through the use of temperature ramping within the thermal desorber. In some embodiments, a substance of interest is detected through a method comprising collecting a sample of a substantially non-volatile substance of interest on a sampling trap; introducing the trap including the substance of interest into a thermal desorber; depositing a reagent on the trap, wherein the reagent increases the volatility of the substance of interest, wherein depositing the reagent includes spraying the reagent on the trap; increasing the temperature within the desorber; vaporizing the substance of interest; transferring the vaporized substance of interest from the desorber into a detector; performing an analysis of the substance of interest; and, detecting the substance of interest.

Figure 9:
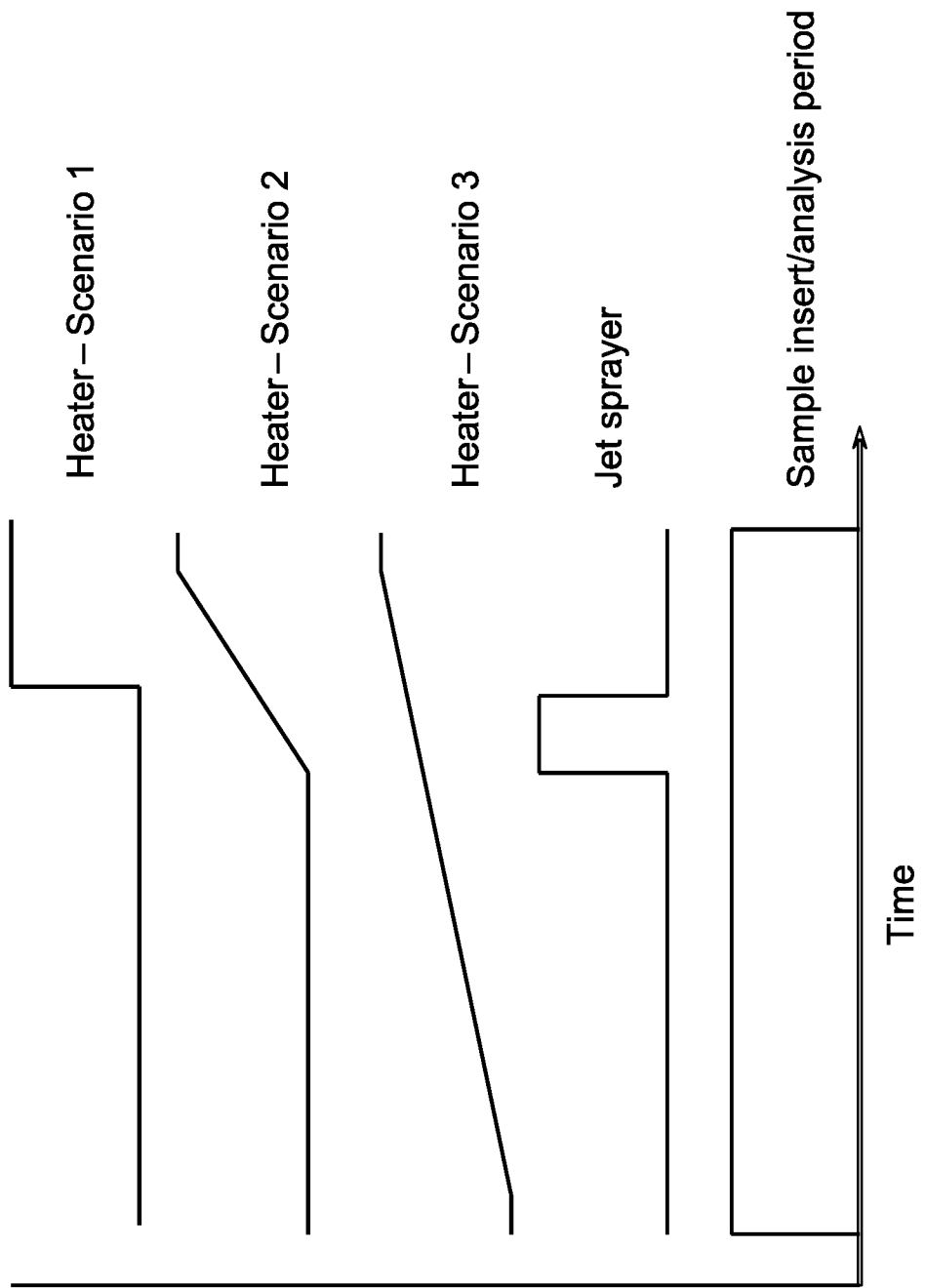
FIG. 9 is an exemplary embodiment of a schematic view of the timing of a jet sprayer versus temperature programming of a desorber in accordance with the present disclosure.

As shown in FIG. 9, heating scenario 1 depicts a step function increase in temperature approximately coincident with the action of the reagent spray jet. In this scenario, the normal, more volatile compounds that are generally detected are allowed to be desorbed and analyzed during the majority or some part of the total sample medium insert and analysis period, thereby not changing the properties of this step for normal analysis. The chemical vaporization reagent spray then defines a second desorption and analysis period for a substantially non-volatile substance that is desorbed at a higher temperature.

In some embodiments, the thermal desorber includes at least one heating plate that is heated by passing a current through the plate to resistive heat the plate. In some embodiments, the heating rate of the plate(s) is programmed to increase during the course of the heating. FIG. 9 depicts various exemplary embodiments of temperature ramping within the thermal desorber in accordance with the present disclosure.

As shown in FIG. 9, in heating scenario 2, the desorber temperature is increased in a ramp manner to allow for best temperature for the multiple compounds that have different melting and boiling points, the least volatile compounds then desorbing later than the more volatile compounds. This programmed temperature ramp also helps separate the detection of the multiple compounds allowing for more specific and selective detection of each compound.

In heating scenario 3, the desorber temperature is increased in a ramp manner starting at the beginning of the sample medium insert and analysis period. This heating scenario then allows for the best temperature for the multiple normal compounds that have different melting and boiling points, the least volatile compounds then desorbing later than the more volatile compounds. This programmed temperature ramp helps separate the detection of the normal multiple compounds allowing for more specific and selective detection of each compound.

In some embodiments of the present disclosure, the temperature within the desorber is increased (i.e., ramped) to a temperature of from about 50° C. to about 400° C., from about 100° C. to about 300° C., or to about 200° C. In some embodiments of the present disclosure, the temperature ramp occurs over a period of time of from about 0 seconds to about 20 seconds, from about 5 seconds to about 15 seconds, or of about 10 seconds.

Other embodiments for timing can also be used. For example, the reagent jet spray can be triggered at the beginning of the sample insertion and analysis period or any time in between the beginning and end of this period. The temperature profile can also be chosen to be any function that enhances the sensitivity and specificity for detection of the normal compounds and the chemically-modified compounds.

Detection Systems

The present disclosure is also directed to substance detection systems. In one embodiment, a substance detection system is provided that comprises a sampling trap including a substantially non-volatile substance of interest; a deposition device including a reagent, the deposition device configured to deposit a reagent onto the sampling trap, wherein the reagent increases the volatility of the substance of interest; a thermal desorber configured to hold the sampling trap; and, an analysis device in flow communication with the desorber and configured to receive the substance of interest and perform an analysis of the substance of interest.

In some embodiments, the deposition device is a sprayer. In some embodiments, the sprayer includes at least one of a bottle, a housing, a calibrated volumetric spray, a standoff device and combinations thereof. In some embodiments, the deposition device includes a substantially closed housing and a reservoir including a vaporized reagent. In some embodiments, the deposition device is an inkjet printer.

In some embodiments, the reagent includes at least one of an acid, water, glycerine, and combinations thereof. In some embodiments, the deposition device is configured to control a temperature of the sampling trap.

In another embodiment, a substance detection system is disclosed that comprises a sampling trap including a substantially non-volatile substance of interest; a thermal desorber configured to hold the sampling trap, wherein the desorber includes a deposition device, the deposition device including a reagent and configured to deposit the reagent onto the sampling trap, wherein the reagent increases the volatility of the substance of interest; and, an analysis device coupled in flow communication with the desorber, the analysis device configured to receive the substance of interest and perform an analysis of the substance of interest.

In some embodiments, the desorber is configured to increase the temperature within the desorber from a temperature of about 50° C. to about 400° C. In some embodiments, the desorber increases the temperature therein over a time period of from about 0 seconds to about 20 seconds. In some embodiments, the desorber is configured to conduct a two-step desorption process within the desorber of the substance of interest, wherein the substance of interest is desorbed for a first period of time, followed by depositing the reagent on the trap, and then the substance of interest is desorbed for a second period of time.

In some embodiments, the deposition device is located within the desorber. In some embodiments, the desorber includes a reagent line coupled to a reagent flow system, the reagent flow system configured to deposit the reagent within the desorber.

Figure 13:
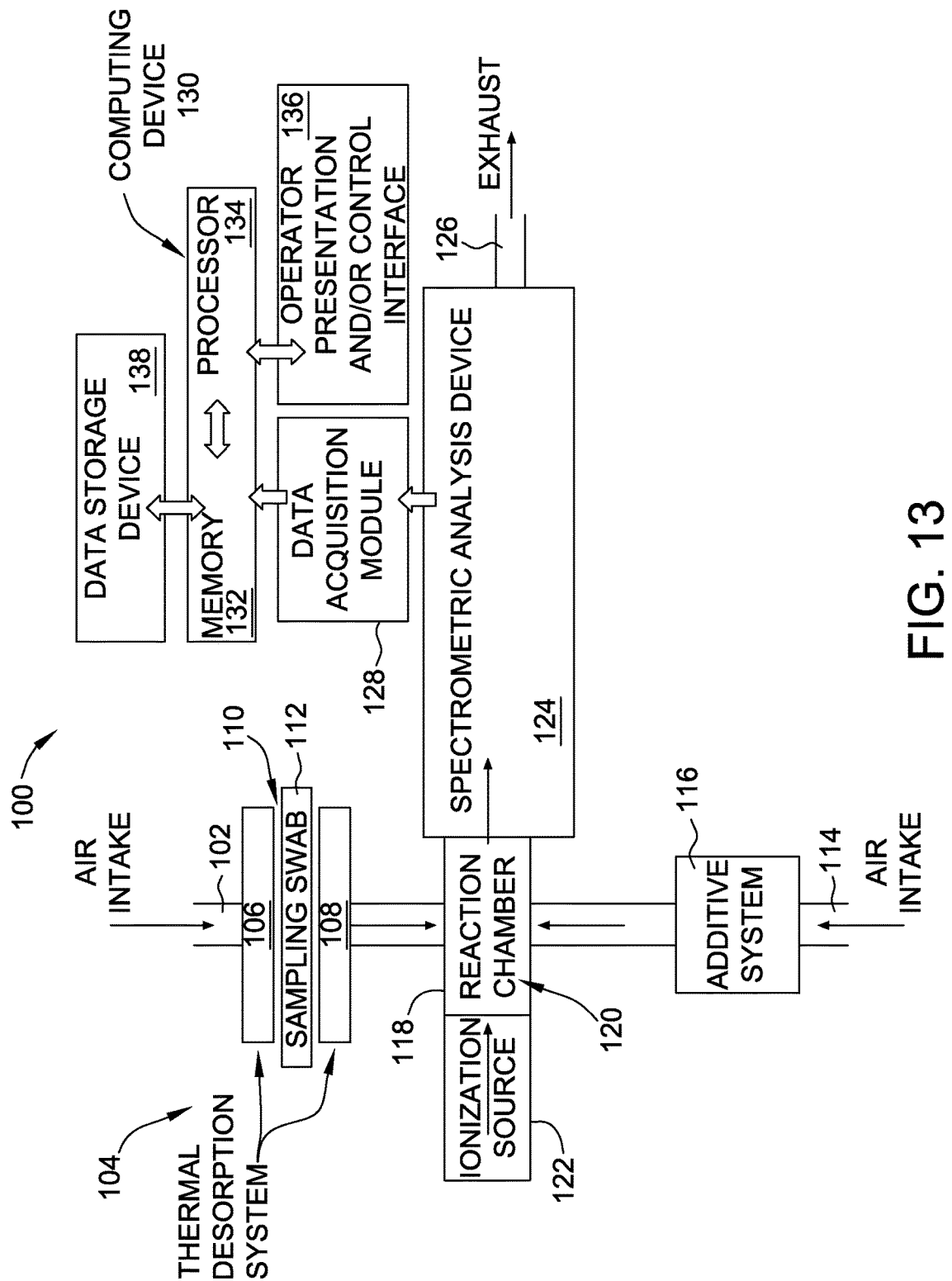
FIG. 13 is an exemplary schematic view of a substance detection system in accordance with the present disclosure.

FIG. 13 is a schematic view of an exemplary substance detection system 100 in accordance with the present disclosure. In the exemplary embodiment, system 100 includes a first air intake device 102. System 100 also includes a sample supply system, i.e., such as a thermal desorption system 104 coupled in flow communication with first air intake device 102. Thermal desorption system 104 further includes a first heating device 106 and a second heating device 108 that define a sampling trap insertion port 110 that receives a sampling trap 112. Alternatively, any configuration of the thermal desorption system 104 that enables operation of system 100 as described herein can be used. In the exemplary embodiment, substance detection system 100 further includes a second air intake device 114 and a reagent (e.g., additive) system 116 coupled in flow communication with second air intake device 114. System 100 further includes a reaction chamber housing 118 defining a reaction chamber 120 (e.g., thermal desorber) coupled in flow communication with thermal desorption system 104 and reagent system 116.

In the exemplary embodiment, system 100 also includes an ionization source 122 coupled in flow communication with reaction chamber 120. Ionization source 122 can be any ionization system that enables operation of system 100 as described herein. Substance detection system 100 further includes a spectrometric analysis device 124 coupled in flow communication with reaction chamber 120. In the exemplary embodiment, spectrometric analysis device 124 is a single quadrupole mass spectrometry device. In alternative embodiments, spectrometric analysis device 124 is any spectrometric analysis system that enables operation of system 100 as described herein, including, without limitation, any mass spectrometry device, any ion mobility spectrometry device, and any differential ion mobility spectrometry device. System 100, in the exemplary embodiment, also includes an exhaust device 126 coupled in flow communication with the spectrometric analysis device 124.

In the exemplary embodiment, substance detection system 100 also includes a data acquisition module 128 coupled to spectrometric analysis device 124. System 100 further includes a computing device 130 coupled to data acquisition module 128. Computing device 130 performs spectrometric analyses of the spectrum data imported from data acquisition module 128. In alternative embodiments, computing device 130 also facilitates control of spectrometric analysis device 124, data acquisition module 128, and any other apparatus associated with substance detection system 100.

As used herein, the term "computer" and related terms, e.g., "computing device", are not limited to integrated circuits referred to in the art as a computer, but broadly refers to a microcontroller, a microcomputer, a programmable logic controller (PLC), an application specific integrated circuit, and other programmable circuits, and these terms are used interchangeably herein. Further, as used herein, the terms "software" and "firmware" are interchangeable, and include any computer program stored in memory for execution by personal computers, workstations, clients and servers.

As used herein, the term "non-transitory computer-readable media" is intended to be representative of any tangible computer-based device implemented in any method or technology for short-term and long-term storage of information, such as, computer-readable instructions, data structures, program modules and sub-modules, or other data in any device. Therefore, the methods described herein may be encoded as executable instructions embodied in a tangible, non-transitory, computer readable medium, including, without limitation, a storage device and/or a memory device. Such instructions, when executed by a processor, cause the processor to perform at least a portion of the methods described herein. Moreover, as used herein, the term "non-transitory computer-readable media" includes all tangible, computer-readable media, including, without limitation, non-transitory computer storage devices, including, without limitation, volatile and nonvolatile media, and removable and non-removable media such as a firmware, physical and virtual storage, CD-ROMs, DVDs, and any other digital source such as a network or the Internet, as well as yet to be developed digital means, with the sole exception being a transitory, propagating signal.

In one embodiment, computing device 130 includes a memory device 132 and a processor 134 operatively coupled to the memory device 132 for executing instructions. In some embodiments, executable instructions are stored in the memory device 132. Computing device 130 is configurable to perform one or more operations described herein by the programming processor 134. For example, processor 134 may be programmed by encoding an operation as one or more executable instructions and providing the executable instructions in memory device 132. In the exemplary embodiment, memory device 132 is one or more devices that enable storage and retrieval of information such as executable instructions and/or other data. Memory device 132 may include one or more computer readable media.

Memory device 132 may be configured to store operational measurements including, without limitation, real-time and historical spectrometric data including, without limitation, sample identification using comparative spectrometric data, isotopic ratios of molecular adduct ions and fragment adduct ions, timing data of elution profiles, thermal desorption profiles, and chromatographic elution profiles for isotopes of adduct ions, and data on ratios of isotopic adduct ions, e.g., relative intensities of isotopic peaks and peak areas of adduct ions in a spectrum, and/or any other type data.

As used herein, the term "real-time" refers to at least one of the time of occurrence of the associated events, the time of measurement and collection of predetermined data, the time to process the data, and the time of a system response to the events and the environment. In the embodiments described herein, these activities and events occur substantially instantaneously.

In the exemplary embodiment, computing device 130, including memory device 132, includes, without limitation, sufficient computer-readable/executable instructions, sufficient data and data structures, algorithms, and commands to facilitate generating comparisons of the data imported from data acquisition module 128 with the stored historical spectrometric data described above. In addition, computing device 130 can either include, or is coupled to, a data storage device 138 that is configured to store such computer-readable/executable instructions, historical data and data structures, algorithms, and commands.

In the exemplary embodiment, substance detection system 100 further includes an operator presentation and/or control interface 136 coupled to computing device 130. Interface 136 presents data, such as spectrometric comparison data to a user (not shown). In some embodiments, interface 136 includes one or more display devices. In some embodiments, interface 136 presents an audible and/or graphical notification upon detection of a substance of interest. Also, in some embodiments, interface 136 facilitates control of computing device 130 and manual data input into computing device 130. Furthermore, in some embodiments, computing device 130 is coupled in communication with one or more other devices, such as another computing device 130, locally or remotely. As such, substance detection system 100 may be networked with other systems and devices such that data transmitted across portions of system 100 may be accessed by any device capable of accessing computing device 130 including, without limitation, desktop computers, laptop computers, and personal digital assistants (PDAs) (neither shown).

EXAMPLES

The following examples describe or illustrate various embodiments of the present disclosure. Other embodiments within the scope of the appended claims will be apparent to a skilled artisan considering the specification or practice of the disclosure as described herein. It is intended that the specification, together with the Examples, be considered exemplary only, with the scope and spirit of the disclosure being indicated by the claims, which follow the Examples.

Example 1

Figure 10A:
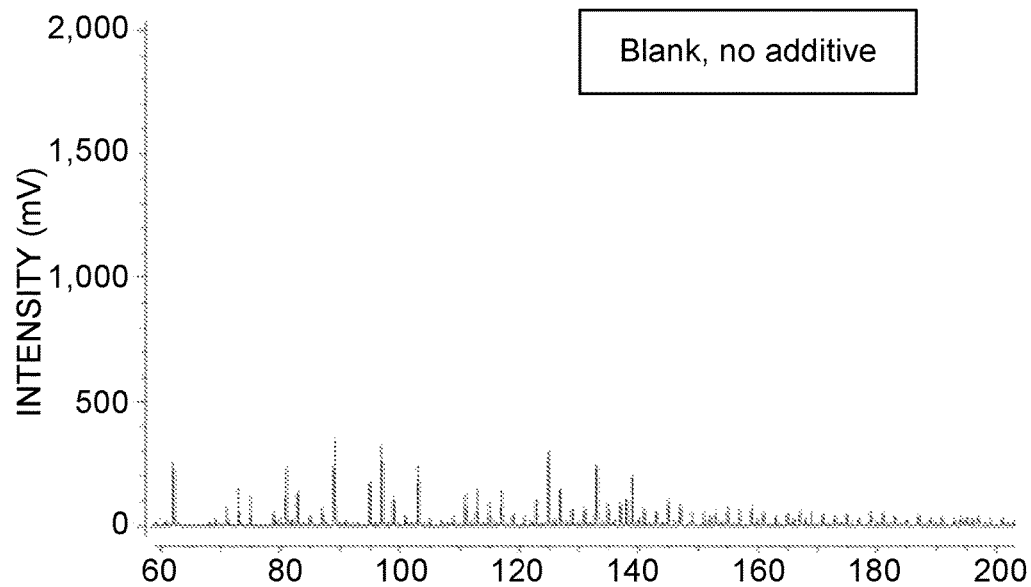
FIG. 10A is an exemplary graph depicting the mass spectrum from a sampling medium without reagent or compound in accordance with the present disclosure.
Figure 10B:
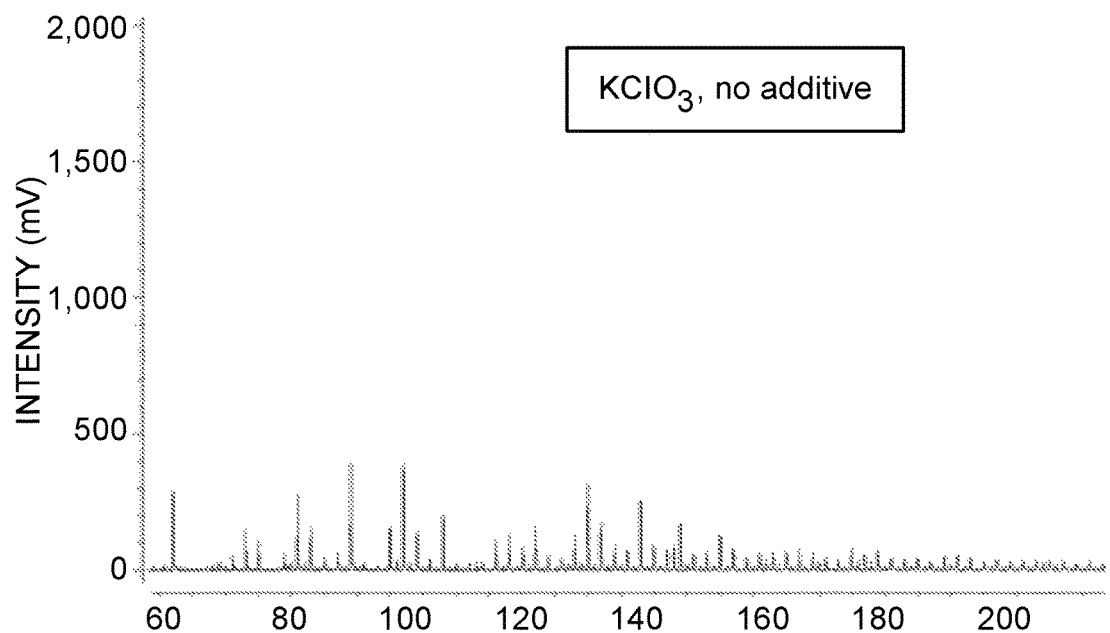
FIG. 10B is an exemplary graph depicting the mass spectrum from a sampling medium without reagent but with an oxidizer salt compound in accordance with the present disclosure.
Figure 10C:
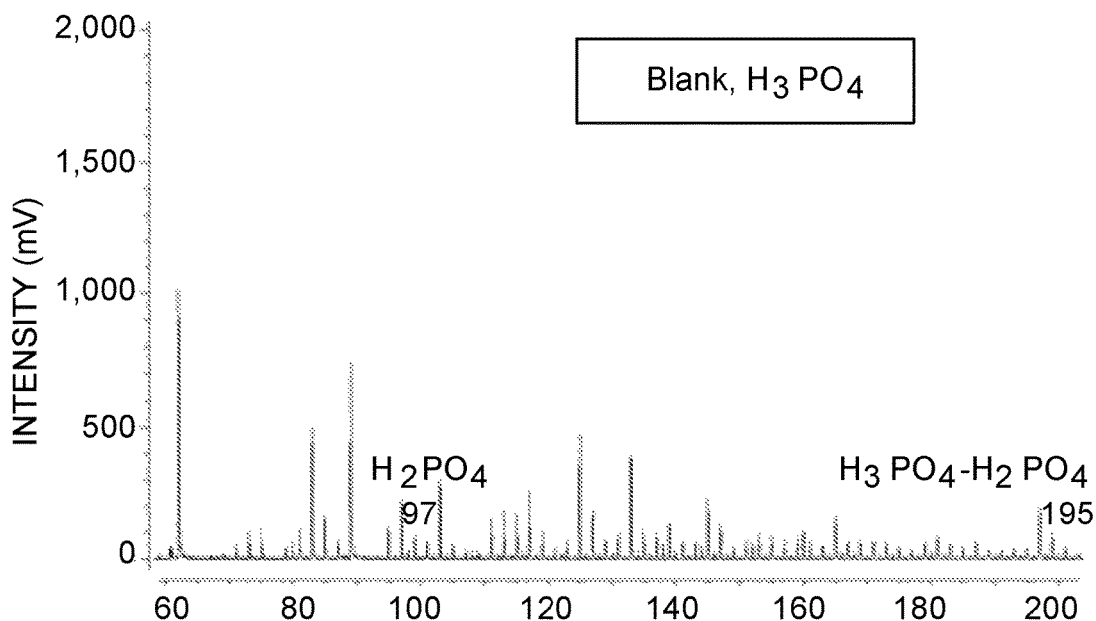
FIG. 10C is an exemplary graph depicting the mass spectrum from a sampling medium with an acid reagent without compound in accordance with the present disclosure.

Example 1 is an exemplary embodiment of the conversion of a substantially non-volatile substance of interest salt into a more volatile acid form. Specifically, FIG. 10A depicts the mass spectrum from a sampling medium without a reagent or a substance of interest. The spectrum consists only of background ion signals. FIG. 10B depicts a mass spectrum from a sampling medium without a reagent but with an oxidizer salt compound—potassium chlorate ($KClO_3$)—deposited thereon. This mass spectrum shows essentially no change from that in FIG. 10A indicating that the salt $KClO_3$ is not detected in its salt form. FIG. 10C depicts the mass spectrum from a sampling medium with an acid reagent—phosphoric acid ($H_3PO_4$)—without potassium chlorate, showing the ion signal that is due to the presence of the acid (being assigned to monomer and dimer ions of the acid). These ion signals, however, do not correspond or overlap with the ions expected from the oxidizer salt $KClO_3$.

Figure 10D:
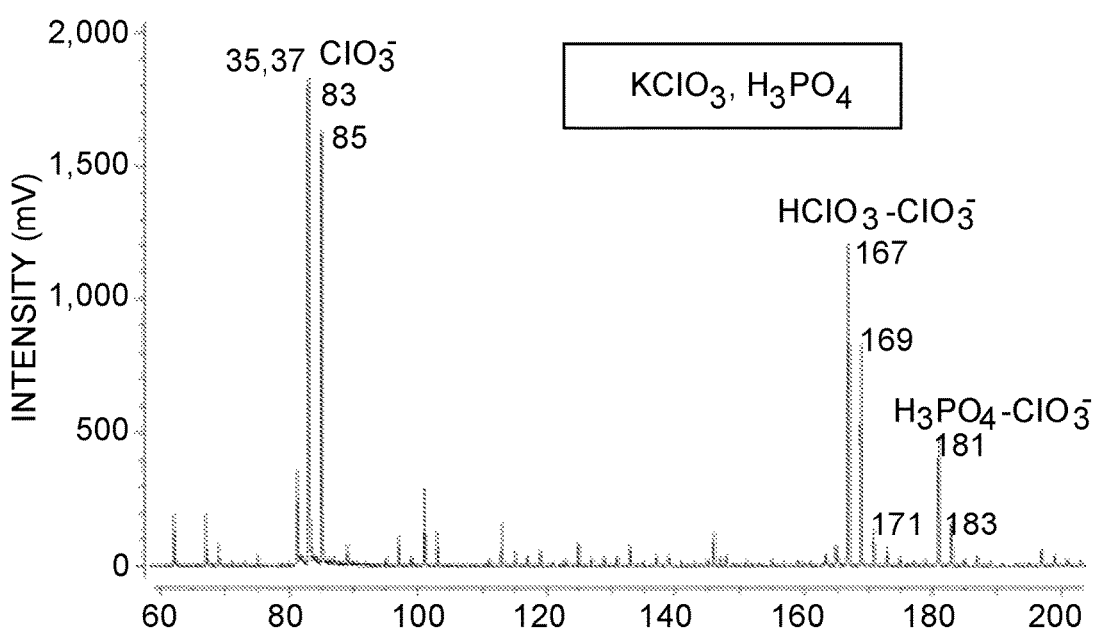
FIG. 10D is an exemplary graph depicting the mass spectrum from a sampling medium with an acid reagent and with an oxidizer salt compound in accordance with the present disclosure.

FIG. 10D depicts the mass spectrum from a sampling medium with the acid reagent $H_3PO_4$ and with the oxidizer salt $KClO_3$ and establishes the ion signals due to the acid form $HClO_3$ giving ion signals for $ClO_3^-$ (monomer) and $HClO_3$—$ClO_3^-$ (dimer). In this example, the oxidizer salt $KClO_3$ in water solution was deposited onto the sampling medium and dried and then the acid reagent $H_3PO_4$ in water solution was sprayed on with a syringe and allowed to dry. The multiple peaks for each group of peaks is due to the isotope distribution of chlorine being in a ratio of about 3:1 for $^{35}Cl$ and $^{37}Cl$.

Thus, as shown in Example 1, potassium chlorate ($KClO_3$), which is a known component of explosives, is a substantially non-volatile compound is not detected in the detection system. When an acidic reagent—phosphoric acid ($H_3PO_4$)—is used to chemically modify the potassium chlorate, the acid increases the volatility of the potassium chlorate and the detection system is able to detect and identify the presence of the modified form of potassium chlorate.

Example 2

Example 2 is an exemplary embodiment of the conversion of a substantially non-volatile substance of interest salt into a more volatile acid form. Specifically, the reducing agent phosphorous trichloride ($PCl_3$) was used as a reagent to chemically modify the substantially non-volatile salt $KClO_3$ into a more volatile form that was detected by an analyzer.

Figure 11A:
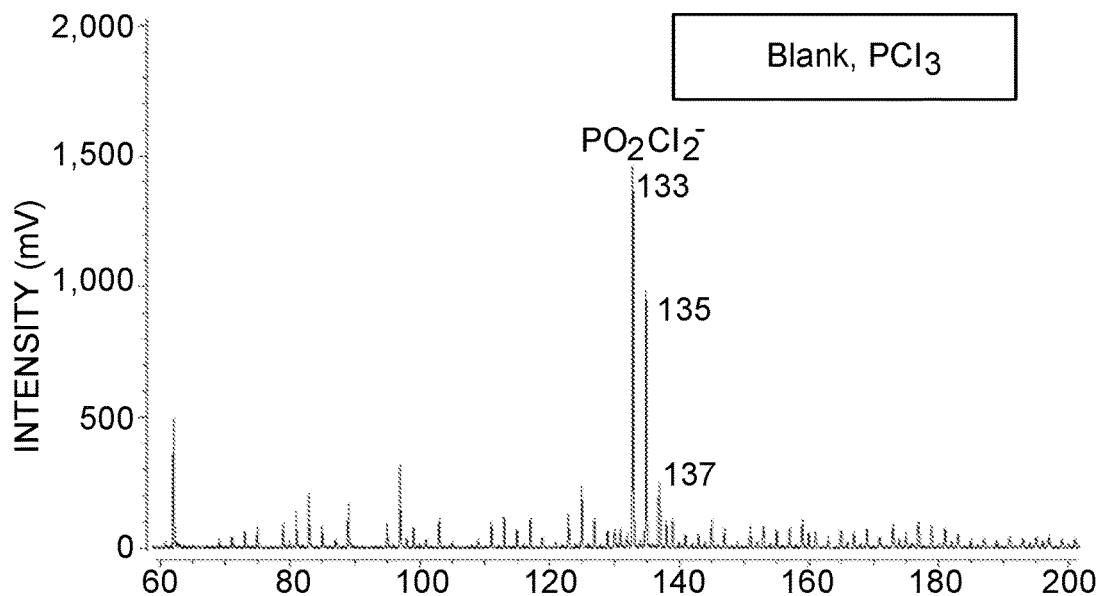
FIG. 11A is an exemplary graph depicting the mass spectrum from a sampling medium with a reducing agent without compound in accordance with the present disclosure.
Figure 11B:
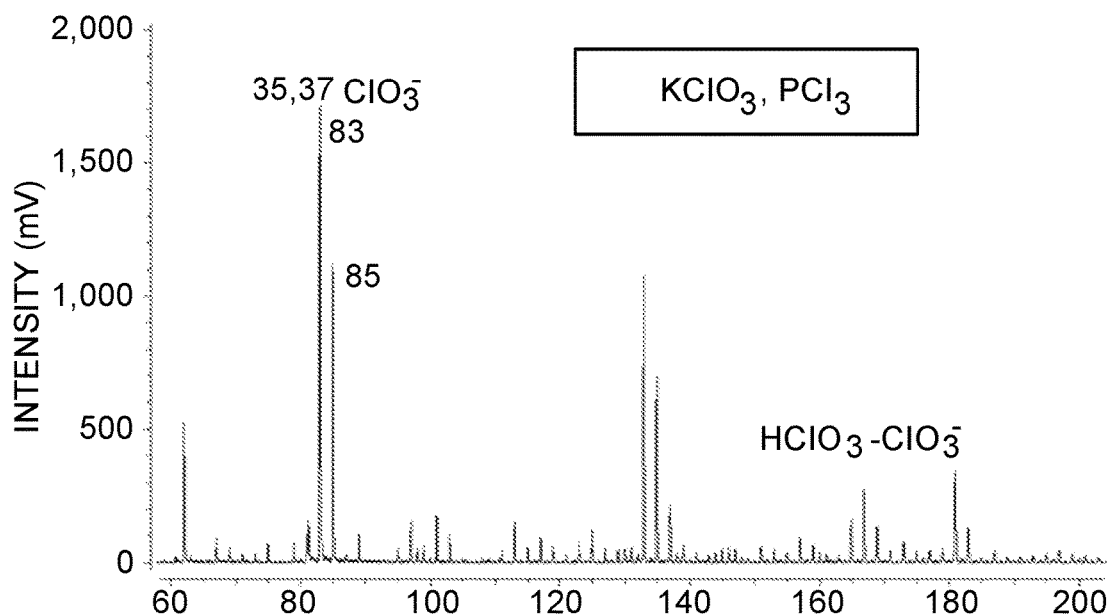
FIG. 11B is an exemplary graph depicting the mass spectrum from a sampling medium with a reducing agent with an oxidizer salt compound in accordance with the present disclosure.

In particular, FIG. 11A FIG. depicts the mass spectrum for the sampling medium containing only the reducing agent $PCl_3$. As shown in FIG. 11A, this gave an ion signal that is specific for $PCl_3$ but not for $KClO_3$. In this particular case, the $PCl_3$ reduces the water vapor in air and becomes oxidized and gave the ion signal $PO_2O_2^-$. As shown in FIG. 11B, the mass spectrum for the sampling medium containing $KClO_3$ produced the specific ion signals $ClO_3^-$ (monomer) and $HClO_3$—$ClO_3^-$ (dimer), similar to the effect of $H_3PO_4$ as shown in FIG. 10D.

Thus, as shown in Example 2, potassium chlorate ($KClO_3$), which is a known component of explosives, is a substantially non-volatile compound that is not detected in the detection system. When a reducing agent reagent—phosphorous trichloride ($PCl_3$)—is used to chemically modify the potassium chlorate, the reducing agent increases the volatility of the potassium chlorate and the detection system is able to detect and identify the presence of the modified form of potassium chlorate.

Example 3

Example 3 is an exemplary embodiment of the conversion of a substantially non-volatile substance of interest salt into a more volatile acid form. Specifically, sulfuric acid ($H_2SO_4$) was used as a reagent to chemically modify the substantially non-volatile salt $KClO_3$ into a more volatile form that was detected by an analyzer.

Figure 12A:
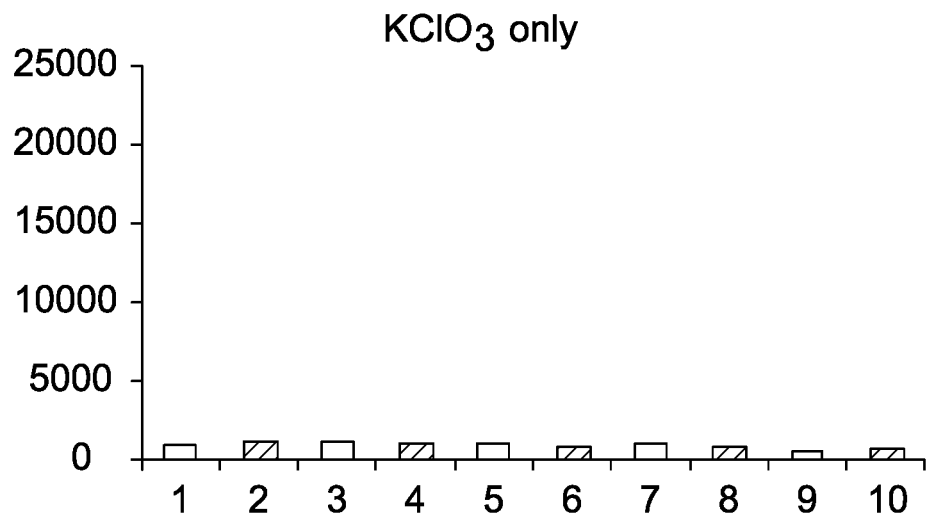
FIG. 12A is an exemplary graph depicting the mass spectrum intensities for the sample ions for repeated sampling from a sampling medium without reagent and with an oxidizer salt compound in accordance with the present disclosure.
Figure 12B:
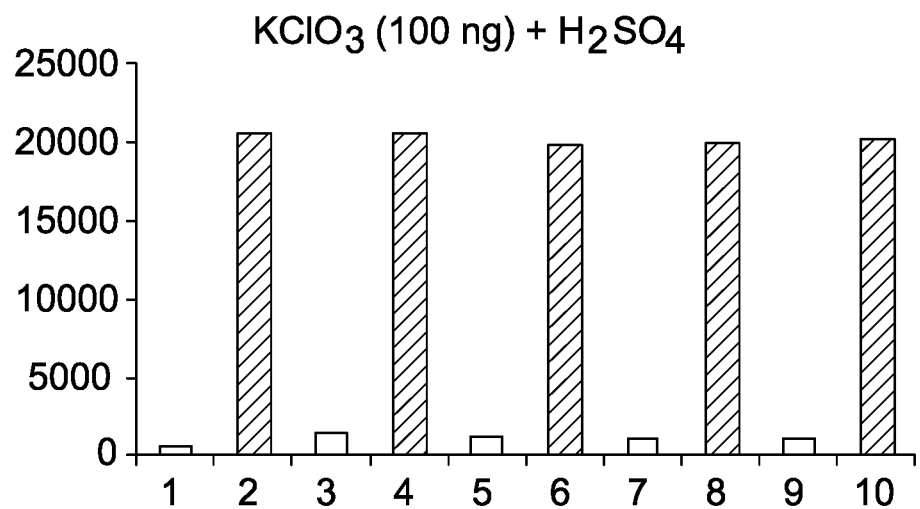
FIG. 12B is an exemplary graph depicting the mass spectrum intensities for ions for repeated sampling from a sampling medium with an acid reagent and with an oxidizer salt compound in accordance with the present disclosure.

In particular, FIGS. 12A and 12B show the results for the reagent sulfuric acid ($H_2SO_4$) assisting in the vaporization of $KClO_3$. These plots show the intensity of the $ClO_3^-$ ion peak for repeated sampling events. FIG. 12A shows the results for no reagent added and deposition of the oxidizer salt $KClO_3$ only on the sampling medium. The odd number intensities (i.e., 1, 3, 5, 7 and 9) are for no oxidizer salt added and the even number intensities (i.e., 2, 4, 6, 8 and 10) are for addition of the oxidizer salt. FIG. 12A indicates that without the acid reagent, no $KClO_3$ is detected. As shown in FIG. 12B, however, when the sulfuric acid was sprayed onto the sampling medium, the chemically-modified form of $KClO_3$ was detected.

Thus, as shown in Example 3, potassium chlorate ($KClO_3$), which is a known component of explosives, is a substantially non-volatile compound that is not detected in the detection system. When an acid reagent—sulfuric acid ($H_2SO_4$)—is used to chemically modify the potassium chlorate, the acid increases the volatility of the potassium chlorate and the detection system is able to detect and identify the presence of the modified form of potassium chlorate.

Exemplary embodiments of substance detection systems for determining the presence of substances of interest, and methods of operating such systems are not limited to the specific embodiments described herein, but rather, components of systems and/or steps of the methods may be utilized independently and separately from other components and/or steps described herein. For example, the methods may also be used in combination with other systems requiring determining the presence of substances of interest, and are not limited to practice with only the substance detection systems and methods as described herein. Rather, the exemplary embodiment can be implemented and utilized in connection with many other substance detection applications that are currently configured to determine the presence of substances of interest.

Although specific features of various embodiments of the disclosure may be shown in some drawings and not in others, this is for convenience only. In accordance with the principles of the disclosure, any feature of a drawing may be referenced and/or claimed in combination with any feature of any other drawing.

Some embodiments involve the use of one or more electronic or computing devices. Such devices typically include a processor or controller, such as a general purpose central processing unit (CPU), a graphics processing unit (GPU), a microcontroller, a reduced instruction set computer (RISC) processor, an application specific integrated circuit (ASIC), a programmable logic circuit (PLC), and/or any other circuit or processor capable of executing the functions described herein. The methods described herein may be encoded as executable instructions embodied in a computer readable medium, including, without limitation, a storage device and/or a memory device. Such instructions, when executed by a processor, cause the processor to perform at least a portion of the methods described herein. The above examples are exemplary only, and thus are not intended to limit in any way the definition and/or meaning of the term processor.

This written description uses examples to disclose the disclosure, including the best mode, and also to enable any person skilled in the art to practice the disclosure, including making and using any devices or systems and performing any incorporated methods. The patentable scope of the disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A method for detecting a substance of interest, the method comprising:
   collecting a sample of a substantially non-volatile substance of interest on a sampling trap;
   depositing a reagent on the trap, wherein the reagent increases a volatility of the substance of interest, wherein depositing the reagent includes spraying the reagent on the trap and wherein the reagent is deposited on the trap at a rate of from about 1 cc/min to about 1,000 cc/min;
   introducing the trap including the substance of interest into a thermal desorber;
   vaporizing the substance of interest;
   transferring the vaporized substance of interest from the desorber into a detector;
   performing an analysis of the vaporized substance of interest; and
   detecting the substance of interest.

2. The method of claim 1, wherein the reagent includes at least one of an organic acid, an inorganic acid or a reducing agent.

3. The method of claim 2, wherein the reagent includes at least one of sulfuric acid, sulfonic acid, phosphonic acid, phosphoric acid or combinations thereof.

4. The method of claim 1, wherein the substance of interest includes at least one of an explosive, an energetic material, a taggant, a narcotic, a toxin, a chemical warfare agent, a biological warfare agent, a pollutant, a pesticide, a toxic industrial chemical, a toxic industrial material, a homemade explosive, a pharmaceutical trace contaminant or combinations thereof.

5. The method of claim 1, wherein the substance of interest includes at least one salt compound.

6. The method of claim 1, wherein the substance of interest includes at least one of sodium nitrate, potassium nitrate, strontium nitrate, barium nitrate, sodium chlorate, potassium chlorate, sodium perchlorate, potassium perchlorate, sodium permanganate, potassium permanganate, or combinations thereof.

7. A substance detection system comprising:
   a sampling trap including a substantially non-volatile substance of interest;
   a deposition device including a reagent, wherein the deposition device is configured to deposit the reagent onto the sampling trap by spraying the reagent on the trap at a rate of from about 1 cc/min to about 1,000 cc/min and wherein the reagent increases a volatility of the substance of interest;
   a thermal desorber configured to hold the sampling trap, wherein the desorber is configured to vaporize the substance of interest; and
   an analysis device in flow communication with the desorber and configured to receive the vaporized substance of interest and perform an analysis of the vaporized substance of interest.

8. The system of claim 7, wherein the reagent includes at least one of an organic acid, an inorganic acid or a reducing agent.

9. The system of claim 8, wherein the reagent includes at least one of sulfuric acid, sulfonic acid, phosphonic acid, phosphoric acid or combinations thereof.

10. The system of claim 7, wherein the substance of interest includes at least one of an explosive, an energetic material, a taggant, a narcotic, a toxin, a chemical warfare agent, a biological warfare agent, a pollutant, a pesticide, a toxic industrial chemical, a toxic industrial material, a homemade explosive, a pharmaceutical trace contaminant or combinations thereof.

11. The system of claim 7, wherein the substance of interest includes at least one of sodium nitrate, potassium nitrate, strontium nitrate, barium nitrate, sodium chlorate, potassium chlorate, sodium perchlorate, potassium perchlorate, sodium permanganate, potassium permanganate, or combinations thereof.

* * * * *